(12) United States Patent
Yamawaki et al.

(10) Patent No.: US 6,569,829 B1
(45) Date of Patent: May 27, 2003

(54) PROCESS FOR PRODUCING LONG CHAIN N-ACYL ACIDIC AMINO ACID

(75) Inventors: Yukio Yamawaki, Nobeoka (JP);
Shinichi Yamamoto, Nobeoka (JP);
Yoshinaga Tamura, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/868,700

(22) PCT Filed: Feb. 18, 1999

(86) PCT No.: PCT/JP99/00730

§ 371 (c)(1),
(2), (4) Date: Sep. 24, 2001

(87) PCT Pub. No.: WO00/40546

PCT Pub. Date: Jul. 13, 2000

(30) Foreign Application Priority Data

Dec. 28, 1998 (JP) ............................................. 10/374039

(51) Int. Cl.⁷ ........................ A01N 37/12; A01N 37/44;
A61K 31/195; C07C 229/00
(52) U.S. Cl. ........................ 510/480; 514/563; 562/571
(58) Field of Search ................................. 562/442, 571;
514/563; 510/480

(56) References Cited

U.S. PATENT DOCUMENTS 3,758,525 A  9/1973  Yoshida et al. .......... 260/402.5
5,098,608 A * 3/1992  Miyazawa et al. .......... 252/546
5,776,438 A * 7/1998  Tokue et al. .................. 424/59

FOREIGN PATENT DOCUMENTS

| EP | 0 844 235 A1 | * 5/1998 |
| JP | 505305 | 1/1975 |
| JP | 51013717 | 2/1976 |
| JP | 3279354 | 12/1991 |
| JP | 3284658 | 12/1991 |
| JP | 597787 | 4/1993 |
| JP | 072747 | 1/1995 |
| JP | 07-002747 | * 6/1995 |
| JP | 1171334 | 3/1999 |
| WO | WO 9703171 | * 1/1997 |

* cited by examiner

Primary Examiner—Richard L. Raymond
Assistant Examiner—Zachary C. Tucker
(74) Attorney, Agent, or Firm—Birch, Stewart, Kolasch & Birch, LLP

(57) ABSTRACT

A process for producing a long chain N-acyl acidic amino acid removes impurities by separating a mixture composed of a long chain N-acyl acidic amino acid containing an inorganic salt and a medium containing water and tertiary butanol into an aqueous layer and an organic layer containing the long chain N-acyl acidic amino acid at a temperature of from 35 to 80° C.

18 Claims, 2 Drawing Sheets

* : POINT A : ORGANIC LAYER AFTER ACID-PRECIPITATION
○ : POINTS B & E
● : POINTS C,D,F & G

PROCESS FOR PRODUCING LONG CHAIN N-ACYL ACIDIC AMINO ACID This application is the national phase under 35 U.S.C. §371 of PCT International Application No. PCT/JP99/00730 which has an International filing date of Feb. 18, 1999, which designated the United States of America and was not published in English.

TECHNICAL FIELD

The present invention relates to a long chain N-acyl acidic amino acid or a salt thereof, and a simple process for producing the same. More specifically, the present invention relates to a long chain N-acyl acidic amino acid or a salt thereof, which has substantially no odor and can be applied even to non-perfume fields, which is diminished in a content of water soluble impurities such as inorganic salts and reaction by-products of free fatty acid, and which is suitable for the production of a detergent or a cosmetic composition, wherein the detergent prepared by incorporating it into a liquid detergent causes neither precipitation nor turbidity.

BACKGROUND ART

An amine or alkali metal salt of a long chain N-acyl acidic amino acid has been extensively used as a surface active agent and an antibacterial agent owing to its surface activity. Particularly, it is extensively used in detergents and cosmetic fields such as quasi-drugs and cosmetics, and in many cases comes in direct touch with the human body. Therefore, it is prohibitive to give users an unpleasant feeling. In such fields, it is frequently required that final products produce no turbidity, and the odor of the final products has an important value to the commodity. Therefore, in using the long chain N-acyl acidic amino acid or a salt thereof in such fields, it is desired to diminish impurities capable of causing turbidity of the final products and those capable of unfavorably affecting the odor of the final products to the utmost.

U.S. Pat. No. 3,758,525 discloses a process for producing a long chain N-acyl acidic amino acid, wherein an acidic amino acid and a long chain fatty acid halide are subjected to condensation reaction in the presence of an alkali using a mixed solvent of 15 to 80% by volume of a hydrophilic organic solvent and 85 to 20% by volume of water, and after the reaction is over, the reaction liquid is adjusted to pH 1, thereby precipitating a crude crystal of a long chain N-acyl acidic amino acid, which is separated by filtration and washed to remove the hydrophilic organic solvent, whereby a desired long chain N-acyl acidic amino acid is obtained. However, the long chain N-acyl acidic amino acid obtained according to said process contains inorganic salts because of insufficient removal thereof, and moreover, the process for separating the long chain N-acyl acidic amino acid as mentioned above is not industrially advantageous from a viewpoint of equipment and operation.

JP-A 51-13717 discloses a process, wherein a reaction liquid obtained by the reaction between an acidic amino acid and a long chain fatty acid halide in a mixed solvent of water and a hydrophilic organic solvent in the presence of an alkali, is adjusted to pH 1 to 6 using a mineral acid at a temperature of from 40° C. to a boiling point of said hydrophilic organic solvent, thereby separating into an aqueous layer and an organic layer containing a desired product, and the hydrophilic solvent is then removed from the organic layer to obtain a long chain N-acyl acidic amino acid. However, according to the process, a content of inorganic salts decreases only to a degree of 1 to 2%, and odoriferous substances originating in the solvent are insufficiently removed. In Examples thereof, it is specifically disclosed that most of the acetone is removed from the organic layer by means of vacuum-heating, and then the remaining acetone is removed in a manner such that water is added to the residue and air is blown to its liquid surface while stirring the liquid at 65° C. However, according to such a solvent removing method as blowing of air to the liquid surface, it is difficult to completely remove the remaining acetone or remove high boiling odoriferous substances mentioned below.

Further, in JP-A 3-284685 of the same applicant as that of U.S. Pat. No. 3,758,525 and JP-A 51-13717, acetone and its aldol-condensation products such as diacetone alcohol and mesityl oxide are named as substances, which remain in the long chain N-acyl acidic amino acid, and which causes an odor in the goods. And it is also disclosed therein that even when the process disclosed in JP-A 51-13717 is used, these odoriferous substances cannot be removed completely and as a result, these are left in the long chain N-acyl acidic amino acid and cause an odor of the products. On such a premise, it is further disclosed to remove these odoriferous substances and salts from an aqueous solution of a salt of the long chain N-acyl acidic amino acid by means of reverse osmosis membrane. However, the process is disadvantageous from a viewpoint of using an expensive membrane separation apparatus, and it cannot be said that the process is simple from an industrial point of view, because the process cannot be carried out without complicated operation control such as control of concentrations and control of membranes.

JP-A 50-5305 discloses that in subjecting an amino acid and a long chain fatty acid halide to condensation in the presence of an alkali, an aqueous lower alcohol is used as a reaction solvent, and as the aqueous lower alcohol, methanol, ethanol, n-propanol, isopropanol, n-butanol, isobutanol and sec-butanol are specifically enumerated in a limited manner. However, all the above-mentioned alcohol are primary or secondary, and therefore in a step of making a pH of the liquid acidic, a dehydration-condensation reaction occurs between the formed long chain N-acyl acidic amino acid and said alcohol solvent, thereby resulting in the production of an ester. In addition, a dehydration-condensation reaction occurs also between said alcohol solvent and a free fatty acid by product through hydrolysis of the raw material of long chain fatty acid halide, thereby producing an ester. The thus produced ester is a compound which is difficult to separate and remove from the long chain N-acyl acidic amino acid.

JP-A 7-2747 also proposes a separation process using a membrane, which is, however, disadvantageous like in the process disclosed in JP-A 3-284685. In Comparative Example of JP-A 7-2747, it is disclosed to directly condense the obtained long chain N-acyl acidic amino acid-containing organic layer, and it is demonstrated that a free fatty acid remarkably increases in the course of said condensing, and the hydrophilic organic solvent is hardly removed.

JP-A 3-279354 discloses a reaction process wherein a mixed solvent of water and an hydrophilic organic solvent consisting of acetone and isopropanol is used to prevent the production of odoriferous components such as diacetone alcohol and mesityl oxide, which are greatly produced when acetone is used singly as the solvent. There is also disclosed a separation process wherein the acidified reaction liquid is subjected to crystallization separation to obtain crystals, which are then dissolved in a hydrophilic organic solvent, and an aqueous solution of a high concentration of sodium sulfate is added thereto, thereby separating into an organic layer and an aqueous layer. However, according to the process, there are left problems such that a step of re-dissolving the crystals once separated by crystallization is troublesome, it is inevitable for the goods to be contaminated with sodium sulfate as far as a large amount of sodium sulfate is used, and it is inevitable to treat a waste liquid containing a high concentration of sodium sulfate. Moreover, even when the mixed solvent of acetone and isopropanol is used as the hydrophilic organic solvent, it is not always sufficient to diminish diacetone and mesityl oxide to a degree such that any additional removal is not required, and as a result, it is still essential to remove these odoriferous components. In addition, with respect to removal of the organic solvent from the organic layer, an Example of said JP-A describes nothing but removal thereof by means of vacuum-heating as a specific removal means, and only describes a content of the acetone-condensation product in the long chain N-acyl acidic amino acid is a trace. It is not clear whether or not it is removed to a degree such that it does not affect the odor of the final product.

As mentioned above, a long chain N-acyl acidic amino acid, which has substantially no odor and which is diminished in a content of water soluble impurities such as inorganic salts and free fatty acids is unknown, and a simple process for producing the same is also unknown.

As a result, any long chain N-acyl acidic amino acid or its salt obtained according to a conventional process always has an odor owing to by-products originating from the reaction solvents, and contains impurities such as inorganic salts and free fatty acids, and therefore there are left problems such that it cannot be applied to a non-perfume system, and when it is incorporated into goods such as a detergent, turbidity or precipitation occurs when stored particularly at a low temperature.

DISCLOSURE OF INVENTION

Under these circumstances, it is an object of the present invention to provide a long chain N-acyl acidic amino acid, which has no effect on perfume of goods, and which has superior stability at low temperature, and it is another object of the present invention to provide a process for producing the long chain N-acyl acidic amino acid.

Generally speaking, using a mixed solvent of a hydrophilic organic solvent and water as a reaction solvent, an acidic amino acid and a long chain fatty acid halide are subjected to condensation in the presence of an alkali to produce a long chain N-acyl acidic amino acid (acylation reaction), and the thus obtained reaction liquid is adjusted to pH 1 to 6 to separate into an organic layer and an aqueous layer, thereby obtaining a long chain N-acyl acidic amino acid-containing organic layer (acid-precipitation separation step). However, the obtained long chain N-acyl acidic amino acid is insufficient in removal of inorganic salts.

The present inventors have undertaken extensive studies to solve the problems of the prior art mentioned above, and as a result, it has been found that a mixed liquid of a long chain N-acyl acidic amino acid and a medium containing at least tertiary butanol and water can be separated into an aqueous layer and a long chain N-acyl acidic amino acid-containing organic layer according to the composition of said three components, and thereby inorganic salts remaining in the long chain N-acyl acidic amino acid can be conveyed into the aqueous layer to be removed (hereinafter the operation being referred to as washing). Thus, tertiary butanol and water are added to the long chain N-acyl acidic amino acid containing inorganic salts to form the three-component system, a composition thereof is appropriately selected, and a separation-removal treatment is repeatedly carried out, whereby a desired content of inorganic salts can be attained.

The present inventors have further found a fact that said tertiary butanol used in the above-mentioned washing step can be advantageously used as a reaction solvent in the acylation reaction step for the production of long chain N-acyl acidic amino acid. In other words, it has been found that when the acylation reaction is carried out using a mixed solvent of tertiary butanol/water, there is observed no production of odoriferous substances such as aldol-condensation products, which are produced when a mixed solvent of acetone/water is used as the reaction solvent as seen in the prior art.

In the case where the obtained long chain N-acyl acidic amino acid is applied to a surface active agent, it is desired to remove the organic solvent used for the production of long chain N-acyl acidic amino acid and impurities originated from the organic solvent as far as possible. However, there is a substantial trace quantity thereof remaining. In practice, diacetone alcohol and mesityl oxide which seem to originate from the acetone solvent can be detected in a now commercially available long chain N-acyl acidic amino acid or its salt. As mentioned above, the diacetone alcohol and mesityl oxide even in a trace quantity causes a bad odor. In addition, even when these odoriferous substances could be removed as far as possible, in the resulting long chain N-acyl acidic amino acid or a salt thereof, an odor such as an odor of fatty acids still remains, and therefore it is difficult to incorporate into non-perfume cosmetics or the like.

When tertiary butanol is used as the reaction solvent, any aldol-condensation products produced when acetone is used are not produced, and therefore, it is permitted to consider the tertiary butanol itself only as the odoriferous substance remaining in products. An odor threshold of tertiary butanol is far higher in comparison with that of the acetone-condensation products such as diacetone alcohol and mesityl oxide, and therefore from a viewpoint of controlling odor, it can be said that the burden of removal is far less when comparing tertiary butanol with acetone.

Turbidity and precipitation caused when the long chain N-acyl acidic amino acid or its salt is incorporated into a liquid detergent or the like, and particularly when the incorporated composition liquid is allowed to stand at a low temperature such as about 5° C., are mainly caused by free fatty acids and inorganic salts contained in the long chain N-acyl acidic amino acid, which are conveyed from the starting materials or produced in the course of the production of long chain N-acyl acidic amino acid. Particularly, the free fatty acids can be obtained by decomposition of the long chain N-acyl acidic amino acid, and when once obtained, the free fatty acids can hardly be separated from the long chain N-acyl acidic amino acid or its salt, and therefore it is important to prevent the yield thereof in the production step. In the production step of the long chain N-acyl acidic amino acid, an increase of the free fatty acids can be observed in a step including a thermal history such as removal of a hydrophilic organic solvent by directly condensing a long chain N-acyl acidic amino acid-containing organic layer, as disclosed in the prior art.

This is because a state of the liquid at the time when the solvent is distillation-removed from the long chain N-acyl acidic amino acid-containing organic layer is bad, in other words, flowability of the liquid is bad, and moreover the liquid is bubbling and in a very unstable state.

Usually, in the case where the long chain N-acyl acidic amino acid is separated from the mixed liquid by distillation-removal of the hydrophilic organic solvent contained in the mixed solvent of water and the hydrophilic organic solvent, it is usual that the distillation is carried out under reduced pressure from a viewpoint of heat supply. However, when the distillation-removal of the hydrophilic organic solvent from the mixed liquid is carried out under reduced pressure, the liquid usually increases its viscosity, and results in a paste having almost no flowability. Here, it has been found that the distillation-removal of the organic substances under such conditions is markedly inferior in efficiency, and almost no odoriferous substance such as acetone and acetone-condensation products including diacetone alcohol and mesityl oxide can be removed.

As mentioned above, when the distillation-removal of the hydrophilic organic solvent contained in the mixed solvent of water and the hydrophilic organic solvent is continued to separate the long chain N-acyl acidic amino acid from the mixed liquid, the liquid increases its concentration and results in a high viscosity. In order to continue the distillation while keeping the flowability of the liquid, it is necessary to raise a temperature of the liquid. Further, to continue the distillation, it sometimes happens that many dispersed bubbles are produced in the liquid. In other words, a bubbling state occurs to make the system very unstable. In such a case, it is necessary to carry out the distillation taking a great amount of time. For example, the bubbling state is controlled in an intermittent manner such that pressure of the system is increased or decreased to prohibit bumping, or the vapor quantity generated is drastically lowered.

Accordingly, in the case where the hydrophilic organic solvent is condensed to be removed in such a manner, the long chain N-acyl acidic amino acid is greatly subjected to thermal history and then decomposes to produce the decomposition products of free fatty acids. When such a salt of the long chain N-acyl acidic amino acid is incorporated into a liquid detergent, because of the increased free fatty acids in the long chain N-acyl acidic amino acid, a cosmetic composition incorporated therewith produces turbidity at a low temperature, and thereby the property essential to the product is markedly impaired.

The present inventors have undertaken extensive studies to attain removal of the hydrophilic organic solvent while preventing the free fatty acid from producing. As a result, it has been found that when the conditions such as a composition of the liquid and a temperature thereof are controlled at the time of removing the hydrophilic organic solvent from a long chain N-acyl acidic amino acid-containing mixed solution of water and the hydrophilic organic solvent, flowability of the liquid in distillation-removal of the solvent can be greatly improved, and viscosity of the liquid during the distillation operation can be kept within a favorable range even while keeping a temperature of the liquid low, and thereby the distillation-removal can be attained to a degree so as to have no effect on an odor of the goods. That is, it is a finding that in removing the hydrophilic organic solvent from the long chain N-acyl acidic amino acid-containing organic layer, the long chain N-acyl acidic amino acid is converted in its alkali salt, and either a solid concentration of the liquid during distillation is held within a fixed range under a fixed temperature condition, or a ratio between the long chain N-acyl acidic amino acid and water in the mixed liquid is maintained within a fixed range under a fixed temperature condition, provided that a composition of the organic solvent in the mixed liquid is not more than 5% by weight.

It is another finding that when the hydrophilic organic solvent is distillation-removed under the above-mentioned conditions, flowability of the liquid can be improved, whereby the liquid temperature of distillation is lowered, a thermal history can be greatly avoided, and production of the free fatty acids owing to decomposition of the long chain N-acyl acidic amino acid can be substantially prohibited. It is a further finding that the thus obtained long chain N-acyl acidic amino acid having a content of the free fatty acid limited to a fixed level can exhibit a markedly superior performance. Thereby, the present invention has been obtained.

That is, the present invention is as follows.

A process for producing a long chain N-acyl acidic amino acid, characterized by comprising a step (washing step) of removing impurities mentioned below by separating a mixture composed of a long chain N-acyl acidic amino acid containing an inorganic salt and a medium consisting essentially of water and tertiary butanol into an aqueous layer and an organic layer containing the long chain N-acyl acidic amino acid at a temperature of from 35 to 80° C.

The above-mentioned process for producing a long chain N-acyl acidic amino acid, wherein the above-mentioned long chain N-acyl acidic amino acid is obtained through the following steps:

1) a step (acylation reaction step) of subjecting an acidic amino acid and a long chain fatty acid halide to condensation in a mixed solvent consisting essentially of water and tertiary butanol in the presence of an alkali, and 2) a step (acid-precipitation separation step) of adjusting the pH of the obtained reaction liquid to from 1 to 6 with use of a mineral acid to separate into an organic layer and an aqueous layer, thereby obtaining an organic layer containing the long chain N-acyl acidic amino acid.

The above-mentioned process, wherein the organic layer containing a long chain N-acyl acidic amino acid obtained in the above-mentioned washing step is subjected to removal of an organic solvent by distillation, in which not less than 1/20 of carboxyl group of the long chain N-acyl acidic amino acid is converted into its alkali salt, and the distillation is carried out under conditions that a temperature of the resulting mixed liquid is controlled so not to exceed 90° C., and water is added to maintain a solid concentration of the mixed liquid to from 5 to 50% by weight.

The above-mentioned process, wherein the organic layer containing a long chain N-acyl acidic amino acid obtained in the above-mentioned washing step is subjected to removal of an organic solvent by distillation, which is carried out under conditions that a temperature of the mixed liquid is controlled not to exceed 90° C., and water is added to maintain a weight ratio between the long chain N-acyl acidic amino acid and water within a range of from 35/65 to 65/35, provided that a content of the organic solvent in the mixed liquid is not more than 5% by weight.

Further, the present invention provides a long chain N-acyl acidic amino acid or a salt thereof having a content of an inorganic salt of not more than 1% by weight, a content of tertiary butanol of from 0.1 to 750 ppm by weight, and/or a content of a free fatty acid of not more than 3.0% by weight, said contents being based on the weight of the long chain N-acyl acidic amino acid. Still further, the present invention provides a detergent or cosmetic composition incorporated with the long chain N-acyl acidic amino acid.

BEST MODE FOR CARRYING OUT THE INVENTION

Figure 1:
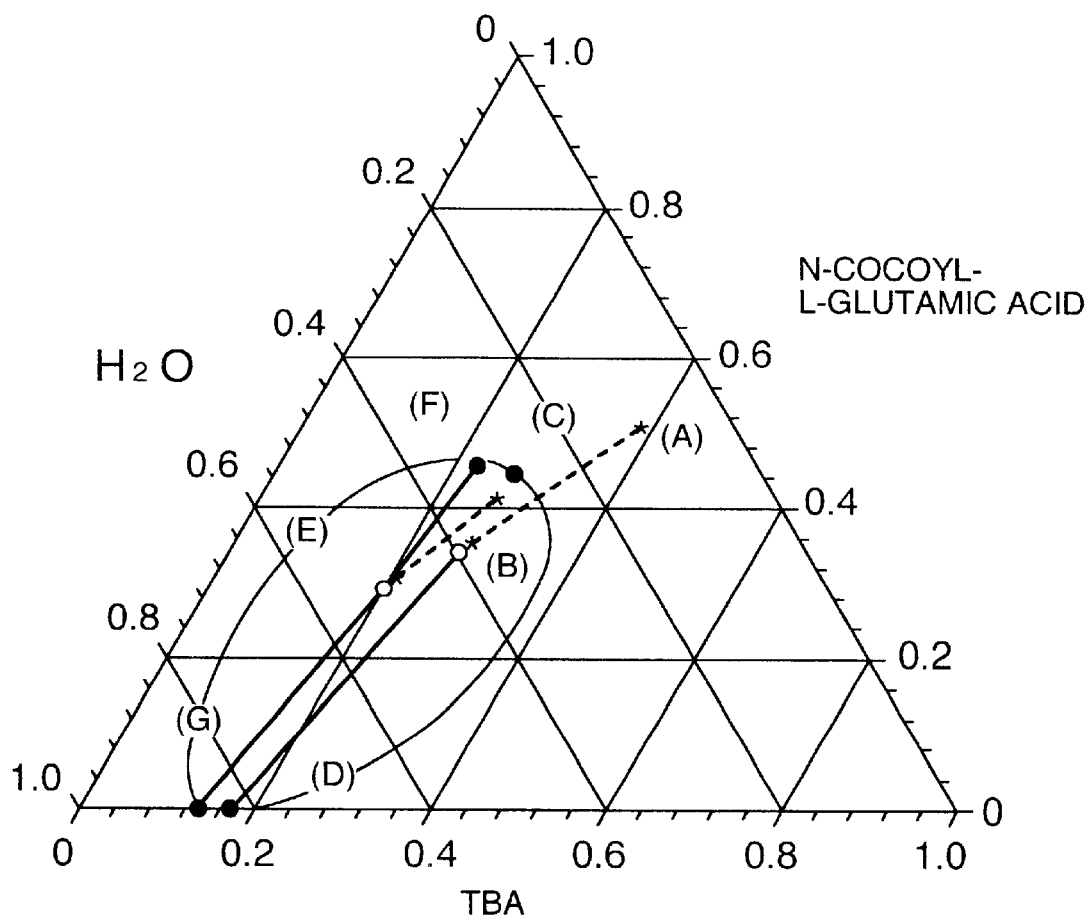
FIG. 1 explains the principle of purification of a long chain N-acyl acidic amino acid in accordance with the present invention, and also to show a composition of causing separation (the region surrounded by a line) among compositions of the above-mentioned amino acid, i.e. N-cocoyl-L-glutamic acid/tertiary butanol/water (in FIG. 1, each scale appearing on each axis being a weight ratio).

The process for producing a long chain N-acyl acidic amino acid in accordance with the present invention has the following steps.

The acylation reaction step in the process in accordance with the present invention is a step of subjecting an acidic amino acid and a long chain fatty acid halide to condensation in a mixed solvent of water and a hydrophilic organic solvent (acylation reaction), thereby obtaining a crude long chain N-acyl acidic amino acid. Although the present invention is explained with reference to a case where tertiary butanol is singly used as the most preferred hydrophilic organic solvent, it is permitted to use tertiary butanol in combination with a small quantity of a conventional hydrophilic organic solvent such as acetone, methanol, ethanol, propanol, isopropanol, butanol, isobutanol, methyl ethyl ketone, tetrahydrofuran, dioxane and the like in a manner such that the effects of the present invention are not injured.

As known, in the water/acetone mixed solvent currently in extensive use for the condensation reaction between an acidic amino acid and a long chain fatty acid halide, acetone is easily dimerized under either acidic or alkaline conditions to produce diacetone alcohol, which is easily dehydrated under further heating to produce mesityl oxide. In short, aldol condensation products of acetone are produced. These cause a bad odor even in trace quantities. For example, in case of a 30 wt % aqueous solution of a monotriethanolamine salt of long chain N-acyl acidic amino acid, it is necessary to suppress the content of diacetone alcohol and mesityl oxide in the aqueous solution to several ppm by weight or less.

The present inventors have noticed a lower alcohol used as a non-ketone hydrophilic solvent in which no aldol condensation occurs. In JP-B 51-38681, it is disclosed that methanol, ethanol, n-propanol, isopropanol, n-butanol, isobutanol and sec-butanol are used. However, the present inventors have confirmed that in the mixed solvent of water/alcohol, under acidic conditions the alcohol easily forms an ester between the acylation reaction product of the long chain N-acyl acidic amino acid and the long chain fatty acid halide, which is as disclosed also in JP-A 7-2747. Notwithstanding, it has been surprisingly found that no ester as mentioned above is produced and no production of other impurities is observed, when as the reaction solvent, the mixed solvent of water/tertiary butanol is used under the conditions defined in the present invention.

From the facts mentioned above, it has been made clear that when the mixed solvent of water/tertiary butanol is used as the acylation reaction solvent, neither aldol condensation products even in a trace quantity causing a bad odor like in a ketone, nor ester between the long chain N-acyl acidic amino acid and the long chain fatty acid halide like in a primary or secondary alcohol is produced.

In the organic layer obtained in the acid-precipitation separation step through the acylation step, an inorganic salt still remains to an extent such that it should be removed. For example, JP-A 51-13717 discloses in its Example that the long chain N-acyl acidic amino acid obtained through distillation-removal of the organic solvent from the organic layer contains an inorganic salt in an amount as large as 1 to 2%. When the long chain N-acyl acidic amino acid containing such a large amount of the inorganic salt is converted, for example, into a 30 wt % aqueous solution of a triethanolamine salt thereof, the turbidity is remarkable at a low temperature, and sometimes precipitation occurs. With respect to the long chain N-acyl acidic amino acid or its salt in accordance with the present invention, a content of inorganic salts is not more than 1% by weight, preferably not more than 0.5% by weight, more preferably not more than 0.1% by weight, based on the weight of the long chain N-acyl acidic amino acid.

When the mixed solvent of water/tertiary butanol is used as the reaction solvent, a further advantage can be observed. In the case where the mixed solvent of water/acetone is used and the acetone recovered from the reaction mixture is reused, for example, the acetone distilled from the organic layer is reused, as mentioned previously, and rectification is required to separate acetone from the aldol condensation products. Whereas, when tertiary butanol is used, the tertiary butanol distilled from the organic layer can be used as is, because such impurities mentioned above are not produced. It is advantageous from a viewpoint of eliminating a process step.

In addition, tertiary butanol can give an advantage also from a viewpoint of handling thereof. When the rectification for the purpose of separating the aldol condensation products is carried out in order to recover and reuse acetone, it is necessary to recover high purity acetone having a substantially low water content. Such acetone has severe inflammability and combustibility and easily forms a combustible gas with air, and therefore it is necessary to take care of its storing and handling on reuse. On the contrary, tertiary butanol forms an azeotrope with water, and therefore in recovering and reusing it, it is impossible to condense tertiary butanol to a degree of a weight ratio of more than tertiary butanol/water=85/15. Thus, tertiary butanol is handled in a state such that a water content is always more than 15% by weight, and therefore easier in storing and handling as compared with acetone.

When the mixed solvent of water/tertiary butanol is used as the reaction solvent, there can be given a further great advantage. That is, when the mixed solvent of water/tertiary butanol is used as the reaction solvent, it is only necessary to add water and/or tertiary butanol to the organic layer obtained through the acid-precipitation separation to adjust a composition of long chain N-acyl acidic amino acid/tertiary butanol/water within a pre-determined range, whereby the organic layer can be separated into an aqueous layer and an organic layer to remove the inorganic salt present in the foregoing organic layer.

On the other hand, in the case of reaction in the mixed solvent of water/acetone, two-phase separation of the organic layer obtained through the acid-precipitation separation into an organic layer and an aqueous layer has never been found regardless of any variations in the organic layer composition or the liquid temperature. While, the reason why in the solvent system of water/acetone, a two-phase separation into the organic layer and the aqueous layer can be seen in the acid-precipitation separation, seems due to a salting out effect of a large amount of inorganic salts such as NaCl and $Na_2SO_4$. Therefore, when the mixed solvent of water/acetone is used, it is indispensable to carry out a process wherein a high concentration of sodium sulfate is added in order to accomplish the separation washing of the organic layer, as disclosed in JP-A 3-279354. In such a case, many salts inevitably remain therein.

From the organic layer obtained by separating into the aqueous layer and the organic layer, tertiary butanol is removed to obtain the long chain N-acyl acidic amino acid. When the long chain N-acyl acidic amino acid or its salt is used for a surface active agent or the like, it is desired to remove the tertiary butanol as far as possible in a conventional manner such as distillation, but it inevitably remains in a trace quantity. In the commercially available long chain N-acyl acidic amino acid or its salt, diacetone alcohol and mesityl oxide, probably originating from the acetone solvent, can be detected. The unremoved diacetone alcohol and the mesityl oxide cause a bad odor. On the contrary, it has been found that tertiary butanol remaining in a trace amount can serve for masking a fatty acid like odor peculiar to the long chain N-acyl acidic amino acid or its salt. Recently, in the fields of cosmetics or the like, there is a tendency of non-perfumed products, and in such a case, materials to be blended are required to have no odor. So far, even when the diacetone alcohol and the mesityl oxide are removed as far as possible, it is impossible to free the long chain N-acyl acidic amino acid or its salt from any odor, and therefore there is left a problem unsolved when it is incorporated into non-perfume cosmetics.

Tertiary butanol itself has a high odor threshold. For example, in the case of a 30% by weight aqueous solution of monotriethanolamine N-cocoyl-L-glutamate, which is one of the long chain N-acyl acidic amino acids, the odor threshold thereof is 150 ppm by weight in said aqueous solution. In other words, a tertiary butanol content in this case corresponds to 750 ppm by weight based on the weight of of N-cocoyl-L-glutamic acid. In the present invention, a content of the tertiary butanol serving for masking the fatty acid like odor of the N-acyl acidic amino acid is from 0.1 to 750 ppm by weight, preferably from 0.1 to 300 ppm by weight, more preferably from 0.1 to 150 ppm by weight, based on the weight of the N-acyl acidic amino acid.

In terms of the 30% by weight aqueous solution of the monotriethanolamine salt, the above-mentioned numerical values are replaced by from 0.02 to 150 ppm by weight, from 0.02 to 60 ppm by weight, and from 0.02 to 30 ppm by weight, respectively. Thus, said aqueous solution has substantially no odor. This is greatly advantageous from an industrial point of view.

The acidic amino acid used as a material in the process in accordance with the present invention is a monoamino dicarboxylic acid having two carboxyl groups and one amino group in the molecule, and the amino group may be substituted with methyl or ethyl to be expressed as N-methyl and N-ethyl. The acidic amino acid includes its optical isomers such as D-isomer, L-isomer and racemic modification. Examples thereof are glutamic acid, aspartic acid, lanthionine, β-methyllanthionine, cystathionine, djenkolic acid, felinine, aminomalonic acid, β-oxyaspartic acid, α-amino-α-methylsuccinic acid, β-oxyglutamic acid, γ-oxyglutamic acid, γ-methylglutamic acid, γ-methyleneglutamic acid, γ-methyl-γ-oxyglutamic acid, α-aminoadipic acid, α-amino-γ-oxyadipic acid, α-aminopimelic acid, α-amino-γ-oxypimelic acid, β-aminopimelic acid, α-aminosuberic acid, α-aminosebacic acid and pantothenic acid. When subjected to acylation reaction, these may be its alkali metal salt and its amine salt.

Preferred examples of the long chain fatty acid halide used as a material in the process in accordance with the present invention are acid chlorides of saturated or unsaturated fatty acids having 8 to 20 carbon atoms, acid bromides thereof and acid iodides thereof, which may be straight, branched or cyclic. Specific examples thereof are halides of straight fatty acids such as caprylic acid, pelargonic acid, capric acid, undecanoic acid, lauric acid, tridecanoic acid, myristic acid, pentadecanoic acid, palmitic acid, margaric acid, stearic acid, nonadecanoic acid and arachic acid; halides of branched fatty acids such as 2-butyl-5-methylpentanoic acid, 2-isobutyl-5-methylpentanoic acid, dimethylocatanoic acid, dimethylnonanoic acid, 2-butyl-5-methylhexanoic acid, methylundecanoic acid, dimethyldecanoic acid, 2-ethyl-3-methylnonanoic acid, 2,2-dimethyl-4-ethyloctanoic acid, methyldocosanoic acid, 2-propyl-3-methylnonanoic acid, methyltridecanoic acid, dimethyldodecanoic acid, 2-butyl-3-methylnonanoic acid, methyltetradecanoic acid, ethyltridecanoic acid, propyldodecanoic acid, butylundecanoic acid, pentyldecanoic acid, hexylnonanoic acid, 2-(3-methylbutyl)-3-methylnonanoic acid, 2-(2-methylbutyl)-3-methylnonanoic acid, butylethylnonanoic acid, methylpentadecanoic acid, ethyltetradecanoic acid, propyltridecanoic acid, butyldodecanoic acid, pentylundecanoic acid, hexyldecanoic acid, heptylnonanoic acid, dimethyltetradecanoic acid, butylpentylheptanoic acid, trimethyltridecanoic acid, methylhexadecanoic acid, ethylpentadecanoic acid, propyltetradecanoic acid, butyltridecanoic acid, pentyldodecanoic acid, hexylundecanoic acid, heptyldecanoic acid, methylheptylnonanoic acid, dipentylheptanoic acid, methylheptadecanoic acid, ethylhexadecanoic acid, ehtylhexadecanoic acid, propylpentadecanoic acid, butyltetradecanoic acid, pentyltridecanoic acid, hexyldodecanoic acid, heptylundecanoic acid, octyldecanoic acid, dimethylhexadecanoic acid, methyloctylnonanoic acid, methyloctadecanoic acid, ethylheptadecanoic acid, dimethylheptadecanoic acid, methyloctyldecanoic acid, methylnonadecanoic acid, methylnonadecanoic acid, dimethyloctadecanoic acid and butylheptylnonanoic acid; halides of straight mono-enoic acids such as octenoic acid, nonenoic acid, decenoic acid, caproleic acid, undecylenic acid, linderic acid, obtusilic acid, laurolenoic acid, tridecenoic acid, tsuzuic acid, myristoleic acid, pentadecenoic acid, hexadecenoic acid, palmitoleic acid, heptadecenoic acid, octadecenoic acid, oleic acid, nonadecenoic acid and gondoic acid; halides of branched mono-enoic acids such as methylheptenoic acid, methylnonenoic acid, methylundecenoic acid, dimethyldecenoic acid, methyldodecenoic acid, methyltridecenoic acid, dimethyldodecenoic acid, dimethyltridecenoic acid, methyloctadecenoic acid, dimethylheptadecenoic acid and ethyloctadecenoic acid; halides of di- or tri-enoic acids such as linoleic acid, linielaidic acid, eleostearic acid, linolenic acid, linolenelaidic acid, pseudoeleostearic acid, parinaric acid and arachidonic acid; halides of acetylenic acids such as octynoic acid, nonynoic acid, decynoic acid, undecynoic acid, dodecynoic acid, tridecynoic acid, tetradecynoic acid, pentadecynoic acid, heptadecynoic acid, octadecynoic acid, nonadecynoic acid and dimethylocatadecynoic acid; and halides of cyclic acids such as methylene-octadecenoic acid, methyleneoctadecanoic acid, aleprolic acid, aleprestic acid, aleprylic acid, alepric acid, hydnocarpic acid, chaulmoogric acid, gorlic acid, α-cyclopentylic acid, α-cyclohexylic acid, α-cyclopentylethylic acid. The long chain fatty acid halide usable for the process in accordance with the present invention includes halides of fatty acids derived from natural fat and oil, provided that the halides are those of a mixed fatty acid containing not less than 80% of the above-mentioned saturated or unsaturated fatty acid having 8 to 20 carbon atoms. For example, there are enumerated halides of coconut oil fatty acid, palm oil fatty acid, palm kernel oil fatty acid, corn oil fatty acid, peanut oil fatty acid, cottonseed oil fatty acid, linseed oil fatty acid, sunflower oil fatty acid, soybean oil fatty acid, sesame oil fatty acid, caster oil fatty acid, olive oil fatty acid, tsubaki oil fatty acid, tallow oil fatty acid, hardened tallow oil fatty acid, lard oil fatty acid, milk oil fatty acid and fish oil fatty acid. The smaller a free fatty acid content in the long chain fatty acid halide, the better.

A molar ratio of long chain fatty acid halide/acidic amino acid is not more than 1.05, preferably not more than 1.0, more preferably not more than 0.98. When the ratio exceeds 1.0, the fatty acid halide is subjected to hydrolysis, thereby producing the free fatty acid.

The tertiary butanol used as the reaction solvent for the acylation reaction step in the process in accordance with the present invention need not have a high purity, and therefore it is permitted to use those containing water or those which are recovered from a reaction system and which are not rectified. A mixing ratio of water/tertiary butanol at the time of the reaction is preferably within a range of from 85/15 to 20/80 by volume.

A concentration of the acidic amino acid to be fed for the acylation reaction step in the process in accordance with the present invention is not particularly limited. However, a viscosity of the reaction liquid increases during the reaction according to the lapse of time, and therefore the feeding concentration should be controlled so as to enable to stir and mix the system even at the time close to completion of the reaction.

As the alkali substances used for the acylation reaction step in accordance with the present invention, for example, there are inorganic bases such as sodium hydroxide, potassium hydroxide, calcium hydroxide and barium hydroxide. It is recommended to maintain the pH during the reaction from 9 to 13.5, preferably from 10 to 13. When the pH is less than 9, the long chain fatty acid halide is hard to react with the acidic amino acid, thereby increase the free fatty acid caused by hydrolysis. When the pH exceeds 13.5, substantially no disadvantages are brought about. However, it is not recommendable from a viewpoint of natural resources, because the amount of alkali is unnecessarily increased with an increase in the amount of an acid consumed in the successive acid-precipitation separation step.

A reaction temperature of the acylation reaction step in the process in accordance with the present invention is not particularly limited. Generally speaking, the reaction temperature can be advantageously lowered with decrease in a production ratio of free fatty acid. However, when the temperature is too low, in the course of the reaction, either viscosity of the reaction liquid is made too high to enable to stir, or it happens that produced materials precipitate, depending upon a kind of the produced long chain N-acyl acidic amino acid or a concentration thereof in the reaction liquid. Therefore, the temperature should be controlled so as not to meet with such disadvantages. It is permitted to change the reaction temperature during the reaction according to the lapse of time. The acylation reaction temperature is usually within a range of from −10 to 70° C., preferably within a range of from −10 to 20° C., more preferably within a range of from −5 to 10° C.

The acylation reaction step in the process in accordance with the present invention can be carried out in a semi-batch manner, wherein the acidic amino acid, alkali and reaction solvent in respective predetermined amounts are fed in a stirring vessel, and thereafter the long chain fatty acid halide is continuously fed therein together with an alkali to make the pH thereof alkaline, or in a manner such that the reaction solvent is fed therein, and thereafter an aqueous alkali solution of the acidic amino acid and the long chain fatty acid halide are continuously fed therein at the same time. After a predetermined degree of the reaction is over, the liquid in the stirring vessel is subjected to the successive acid-precipitation separation step. In feeding the long chain fatty acid halide into the stirring vessel, it may be sprayed or fed so as to be introduced into the liquid. Alternatively, it may be carried out in a continuous manner, wherein using the stirring vessel or a tubular reactor, the reaction solvent, the aqueous alkali solution of the acidic amino acid and the long chain fatty acid halide are continuously fed therein, while continuously taking out the reaction liquid, which is then subjected to the successive acid-precipitation separation.

In the process in accordance with the present invention, it is important to conduct the condensation reaction between the acidic amino acid and the long chain fatty acid halide under stirring or under a condition that liquids are sufficiently mixed. Under an insufficient stirring condition, selectivity of the condensation reaction between the acidic amino acid and the long chain fatty acid halide is lowered to increase a production of the free fatty acid owing to hydrolysis of the long chain fatty acid halide. With respect to the reason thereof, it seems that the reaction system forms two phases, the reaction proceeds at an interface of the long chain fatty acid halide dispersed in the liquid, and therefore renewal of the interface is essential for maintaining the reaction selectivity.

The stirring is carried out necessarily under not less than 0.2 kW/m$^3$ in terms of a stirring power. Even under a stirring power lower than that, it is possible to obtain the long chain N-acyl acidic amino acid, but it is not sufficient to obtain the long chain N-acyl acidic amino acid having a content of the free fatty acid of not more than 3% by weight, which is one embodiment of the present invention. The stirring power is preferably not less than 0.3 kW/m$^3$, more preferably not less than 0.5 kW/m$^3$.

The acid-precipitation separation step in the process in accordance with the present invention is a step of adjusting the acylation reaction liquid to pH 1 to 6 using a mineral acid such as hydrochloric acid and sulfuric acid, thereby separating it into two layers of an organic layer and an aqueous layer to obtain the desired organic layer. In the acylation reaction liquid, the produced long chain N-acyl acidic amino acid exists in the form of its alkali salt. By adding a mineral acid thereto, a part or the whole of the carboxyl group appended to the long chain N-acyl acidic amino acid is converted to a free acid, and at the same time the reaction liquid is separated into an organic layer and an aqueous layer.

The pH at the time of the acid-precipitation separation can be changed with change of dissociation condition of the carboxyl group, according to which the separation condition, namely a weight ratio between the organic layer and the aqueous layer, and a removing degree of the inorganic salts are changed, and therefore it is recommended to carry out the acid-precipitation separation step preferably at pH 1 to 3, more preferably at pH 1 to 2.5.

A temperature of the acid-precipitation separation is from 35° C. to a boiling point of the hydrophilic organic solvent, for example, 80° C. when the hydrophilic organic solvent is tertiary butanol. Preferably, it is from 40 to 70° C. When the temperature is lower than 35° C., the time before reaching a separation equilibrium may be prolonged, or a remarkable amount of the inorganic salt remains in the organic layer even at a stage of the equilibrium, or no separation occurs depending upon a kind of the long chain N-acyl acidic amino acid or its concentration in the liquid. A boiling point of the azeotropic composition of water/tertiary butanol is about 80° C. under atmospheric pressure, and at a temperature exceeding 80° C., boiling occurs, and as a result it becomes necessary to carry out the separation under increased pressure. This is disadvantageous, because a specific apparatus is required.

The washing step in the process in accordance with the present invention is a step of conveying water soluble impurities present in the organic layer obtained in the acid-precipitation separation step to an aqueous layer by means of liquid-liquid extraction, thereby reducing the impurities. More specifically, to the organic layer acid-precipitation separated, water and/or tertiary butanol are(is) added to adjust a composition of long chain N-acyl acidic amino acid/tertiary butanol/water, whereby the water soluble impurities in the organic layer, mainly inorganic salts produced during the reaction and in the acid-precipitation separation step, are conveyed to an aqueous layer through the liquid-liquid extraction.

At this time, respective concentrations of the foregoing three components are adjusted so as to make the long chain N-acyl acidic amino acid from 0.001 to 55% by weight, tertiary butanol from 5 to 45% by weight and water from 20 to 99% by weight, thereby causing the separation. By making good use of such a liquid separation, it is possible to remove the inorganic salts remaining in the long chain N-acyl acidic amino acid-containing organic layer.

Behavior of the separation is expressed as an example with reference to a triangular coordinate relating to a composition (% by weight) of N-cocoyl-L-glutamic acid/tertiary butanol/water, wherein a composition capable of causing the separation is a region surrounded by line in FIG. 1 (separation region).

As far as the composition is within such a region, the mixed liquid can be separated into two layers of the N-cocoyl-L-glutamic acid-containing organic layer and an aqueous layer. Therefore, when respective compositions are determined so as to enter within such a region, purification of the organic layer can be conducted many times. For example, the purification can be repeated until a content of the inorganic salts in the organic layer reaches a desired degree. This is illustrated in more detail with reference to an example of FIG. 1

The scale appearing on each axis is a weight ratio. When a composition of an organic layer after the acid-precipitation separation is designated with Point A, water is added to obtain a composition designated with Point B, whereby the above-mentioned organic layer is separated into an organic layer and an aqueous layer, whose compositions are designated with Point C and Point D, respectively. When water is further added to the organic layer of the composition designated with Point C to obtain a composition designated with Point E, the organic layer is separated into two layers of an organic layer and an aqueous layer, whose compositions are designated with Point F and Point G, respectively. If the content of inorganic salts in the organic layer of the composition designated with Point F reduces satisfactorily to a desired degree, the washing step is completed. If the washing is incomplete, an additional separation operation is carried out in a similar manner.

In the present invention, the content of inorganic salts is controlled to be not more than 1% by weight, preferably not more than 0.5% by weight, more preferably not more than 0.1% by weight, based on the weight of the long chain N-acyl acidic amino acid. In the case where the content of the inorganic salts in a salt of the long chain N-acyl acidic amino acid is more than 1% by weight based on the weight of the long chain N-acyl acidic amino acid, there results precipitation or turbidity at a low temperature, when the salt of the long chain N-acyl acidic amino acid is incorporated into a liquid detergent.

In the washing step of the process in accordance with the present invention, it is recommended to concentrate the tertiary butanol as much as possible to realize the separation, because the time before reaching separation equilibrium can be shortened by increasing the concentration of tertiary butanol within said separation region.

In the washing step in the process in accordance with the present invention, the washing temperature is from 35 to 80° C., preferably from 40 to 70° C. When the temperature is lower than 35° C., the time before reaching a separation equilibrium may be prolonged, or a remarkable amount of the inorganic salts remains in the organic layer even at a stage of the equilibrium, or no separation occurs depending upon a kind of the long chain N-acyl acidic amino acid or its concentration in the liquid. A boiling point of the azeotropic composition of water/butanol is about 80° C. under atmospheric pressure, and at a temperature exceeding 80° C., boiling occurs, and as a result it becomes necessary to carry out the separation under increased pressure. This is disadvantageous, because a specific apparatus is required.

As made clear from the relation between the long chain N-acyl acidic amino acid and the mixed solvent of water and tertiary butanol, according to the washing step in accordance with the present invention, it is possible to reduce the inorganic salt impurities to a desired degree also with respect to a long chain N-acyl acidic amino acid containing impurities such as inorganic salts, which is produced according to a process other than that in accordance with the present invention.

As to a solvent distillation removal step in the process in accordance with the present invention, in removing the hydrophilic organic solvent from the long chain N-acyl acidic amino acid-containing organic layer, a part of the carboxyl group of the long chain N-acyl acidic amino acid is neutralized before distillation removal of the solvent (neutralization solvent distillation removal) or not (non-neutralization solvent distillation removal).

First of all, an illustration is given for the neutralization solvent distillation removal step. According to the process, the hydrophilic organic solvent is distilled off in the presence of a salt of the long chain N-acyl acidic amino acid.

An alkali salt thereof is not particularly limited. Examples thereof are salts of alkali metals such as sodium, potassium and lithium, salts of alkaline earth metals such as calcium and magnesium, aluminum salts, zinc salts, ammonium salts, salts of organic amines such as monoethanolamine, diethanolamine, triethanolamine and triisopropanolamine, and salts of basic amino acids such as arginine and lysine.

In order to convert the long chain N-acyl acidic amino acid into its organic amine salts or its alkali metal salts, for example, it is only needed to add an alkali or its aqueous solution. In converting into a salt of the long chain N-acyl acidic amino acid, it is recommended to add the alkali so as to convert not less than 1/20 of the carboxyl group content of the long chain N-acyl acidic amino acid into its alkali salt. When the proportion of the alkali salt is less than 1/20 of the carboxyl group content, the addition effect of the alkali is slight and as a result, flowability of the mixed liquid cannot be improved. It is preferred to make the proportion of the alkali salt at least 1/10 or more of the carboxyl group content. It is more preferred to make the proportion of the alkali salt at least 1/3 or more of the carboxyl group content.

In the neutralization solvent distillation removal step in accordance with the present invention, a temperature of the mixed liquid at the time of distillation is controlled as not to exceed 90° C. When it exceeds 90° C., there is an accelerated thermal hydrolysis reaction of the long chain N-acyl acidic amino acid or its salt, and the resulting product has inferior quality. Preferably, the temperature is controlled as not to exceed 80° C. More preferably, it is controlled as not to exceed 70° C. In view of controlling the liquid temperature under such a condition, with respect to distillation pressure, it is recommended to use reduced pressure while keeping it at a fixed degree.

Under such conditions, the distillation removal of the hydrophilic organic solvent can be attained while substantially prohibiting the free acid from producing.

Here, a pressure-boiling point curve in the system of long chain N-acyl acidic amino acid/hydrophilic organic solvent is consistent with a pressure-boiling point curve in the system of hydrophilic organic solvent/water. The long chain N-acyl acidic amino acid is not concerned entirely in the pressure-boiling point curve, and therefore, when a temperature of the mixed liquid is determined, an operation pressure can be determined from the pressure-boiling point curve in the system of hydrophilic organic solvent/water.

In the process in accordance with the present invention, water is also lost with the hydrophilic organic solvent during the distillation removal, and therefore, as the case may be, there is required a means for preventing the long chain N-acyl acidic amino acid from extraordinarily condensing. Such a means, for example, can be to intermittently or continuously supply water to the solution during the distillation removal, wherein water includes cool water, hot water and steam. In the case where the process in accordance with the present invention is carried out in a stirring vessel, such a means of blowing steam is effective from a viewpoint of heat supply, because steam makes good use of latent heat.

One of important factors in the neutralization solvent distillation removal in accordance with the present invention is to maintain a solid concentration in the liquid from 5 to 50% by weight during distillation, for example, according to the means mentioned above. When the solid concentration is higher than 50% by weight, there is the possibility of high viscosity of the liquid or solidification. When the solid concentration is lower than 5% by weight, the concentration of the hydrophilic organic solvent is lowered to decrease a distillation efficiency. Moreover, a further concentration is disadvantageously required in the case where the final product requires a solid concentration higher than that. It is preferable to maintain the solid concentration from 20 to 40% by weight. It is more preferable to maintain the solid concentration from 25 to 35% by weight.

Secondly, an illustration is given for the non-neutralization solvent distillation removal step. According to the process, the hydrophilic organic solvent is distillation-removed without neutralization of the long chain N-acyl acidic amino acid.

In the non-neutralization solvent distillation removal step in accordance with the present invention, it is important to maintain a weight ratio between the long chain N-acyl acidic amino acid and water within a range of from 35/65 to 65/35, provided that a composition of the hydrophilic organic solvent in the solution is not more than 5% by weight, and to maintain a solution temperature from 75 to 100° C.

A temperature of the mixed liquid at the time of distillation is controlled not to exceed 90° C. When it exceeds 90° C., there is an accelerated thermal hydrolysis reaction of the long chain N-acyl acidic amino acid or its salt, and the resulting product deteriorates in quality. Preferably, the temperature is controlled as not to exceed 80° C. More preferably, it is controlled not to exceed 70° C. With respect to distillation pressure, it is recommended to carry out distillation under a fixed degree of reduced pressure, in view of controlling the liquid temperature.

When water decreases during distillation to an amount smaller than 65/35 in terms of the weight ratio between the long chain N-acyl acidic amino acid and water, provided that a composition of the hydrophilic organic solvent in the solution is not more than 5% by weight, the solution easily becomes paste. However, when water increases to an amount larger than 35/65 in terms of the weight ratio between the long chain N-acyl acidic amino acid and water, the solution easily becomes agar. In any case, flowability of the liquid is lost. Although the reason is not clear, such a tendency is remarkable when the long chain N-acyl acidic amino acid having an acyl group is derived from the foregoing mixed fatty acid, namely an acyl group having a distribution of its carbon atoms.

In the non-neutralization solvent distillation removal step in accordance with the present invention, water is also lost with the hydrophilic organic solvent during the distillation removal, and therefore, as the case may be, there is required a means for keeping the weight ratio of long chain N-acyl acidic amino acid/water within a range of from 35/65 to 65/35. As a means for keeping the weight ratio within the above-mentioned range, for example, it is permitted to intermittently or continuously supply water to the solution during the distillation removal. In the case where the process in accordance with the present invention is carried out in a stirring vessel, such a means of blowing steam is effective from a viewpoint of heat supply, because the steam makes good use of latent heat.

By carrying out the solvent removal step as mentioned above, the distillation removal of the hydrophilic organic solvent can be attained while substantially prohibiting the free fatty acid from producing.

In view of a liquid state at the time of solvent removal, it is preferred to adopt the neutralization solvent distillation removal step, because the distillation removal of the solvent from the neutralized liquid minimizes any thermal history.

For carrying out the neutralization and non-neutralization solvent distillation removal steps in accordance with the present invention more efficiently from an industrial point of view, the following process is effective.

In carrying out the present invention to distillation-remove the hydrophilic solvent from the mixed liquid of the mixed solvent of water and the hydrophilic organic solvent, in which the long chain N-acyl acidic amino acid is contained, it is effective to adopt an evaporation technique using a spray evaporator, wherein the mixed liquid is sprayed into an evaporation vessel as a vapor-liquid mixed-phase flow, thereby evaporating the hydrophilic organic solvent, as disclosed in, for example, JP-A 5-49801.

According to this technique, the liquid taken out from the lower part of the evaporation vessel is circulated to a heat exchanger with the aid of a pump, and thereafter the liquid is superheated to a predetermined degree and is sprayed into the evaporation vessel through a line provided to the upper part of the evaporation vessel, thereby evaporating the solvent. Characteristic features of the manner are as follows.
1) At a vapor phase portion of the evaporation vessel, there is(are) provided one or several line end(s) of an almost cylindrical form toward the liquid surface, which line end(s) is(are) connected to the line provided to the upper part of the evaporation vessel.
2) By controlling both a flow rate of the liquid in the heat exchanger and a degree of excess heat at an outlet of the heat exchanger, the superheated liquid sent from the heat exchanger is evaporated to form the vapor-liquid mixed-phase flow before reaching the line end.
3) The remaining excess heat in the droplet sprayed from the line end is released before reaching the liquid phase inside of the evaporation vessel.

The flow form of the vapor-liquid mixed-phase flow is classified as shown in the flow constitutional diagram of vertical vapor-liquid two-phase flow in, for example, No.5 revised edition, pages 272 and 273 of Kagaku Kogaku Binran (Chemical Engineering Handbook).

When a liquid capable of bubbling is distilled in the above-mentioned manner, the vapor-liquid mixed-phase flow at the line end is formed into an intermittent flow or a circulating flow. In practice, the flow form can be adjusted by controlling both a linear velocity of the liquid at the line end and a temperature difference (degree of excess heat) between a liquid temperature at the outlet of superheater and a boiling temperature of the liquid under operation pressure in the evaporation can.

In addition, according to the manner of using such a spray evaporator, it is possible to remove the high boiling aldol condensation products to a degree of no influence, which condensation products are produced when the acylation reaction step is carried out in the mixed solvent of acetone/water, and which condensation products remaining in goods are so far difficult to be removed.

In carrying out the solvent distillation removal in accordance with the present invention for distillation-removing the hydrophilic organic solvent from the mixed liquid of water and the hydrophilic organic solvent, in which the long chain N-acyl acidic amino acid is contained, a thin-film type evaporator can also be used.

The thin-film type evaporator can be exemplified by a falling thin-film type evaporator, wherein a liquid is allowed to flow down in a liquid-film form and heated, thereby evaporating a solvent, and a vapor and a condensed liquid are separated from each other in an evaporation vessel, a centrifugal thin-film type evaporator, wherein a liquid is spread on a heating surface with the aid of centrifugal power, thereby forming a thin-film, and a stirring thin-film type evaporator, wherein a liquid thin-film is formed on a heating surface by contacting the heating surface with a stirring blade.

In the long chain N-acyl acidic amino acid or a salt thereof in accordance with the present invention, it is permitted to remove the hydrophilic organic solvent so as not to affect the odor of the product. In the solvent distillation removal step, a content of tertiary butanol is made to be from 0.1 to 750 ppm by weight, more preferably from 0.1 to 300 ppm by weight, much more preferably from 0.1 to 150 ppm by weight based on the weight of the N-acyl acidic amino acid.

The present invention relates to a long chain N-acyl acidic amino acid or a salt thereof, and an illustration thereof is given as follows.

By carrying out the process in accordance with the present invention, substantially no free fatty acid is produced in the production step of the long chain N-acyl acidic amino acid in accordance with the present invention, or if any, a quantity thereof can be restrained to be markedly small. In addition, the obtained long chain N-acyl acidic amino acid has substantially no odor and a very small content of inorganic salts, and therefore is in a high purity and remarkably useful for industries.

In the long chain N-acyl acidic amino acid or a salt thereof in accordance with the present invention, a content of the inorganic salts is not more than 1% by weight based on the weight of the long chain N-acyl acidic amino acid, and a content of tertiary butanol is from 0.1 to 750 ppm by weight based on the weight of the long chain N-acyl acidic amino acid.

When the inorganic salts exceeds 1% by weight based on the weight of long chain N-acyl acidic amino acid, precipitation and turbidity occur at a low temperature when an aqueous solution of a salt of the long chain N-acyl acidic amino acid or a cosmetic composition prepared by incorporating a salt of the long chain N-acyl acidic amino acid into a liquid detergent. The content of the inorganic salts is preferably not more than 0.5% by weight, more preferably not more than 0.1% by weight.

When tertiary butanol is less than 0.1 ppm by weight based on the weight of the long chain N-acyl acidic amino acid, the masking effect is not sufficient. Whereas, when it is more than that, the masking effect can be observed, but there is also created a problem from the odor of tertiary butanol.

Such a long chain N-acyl acidic amino acid or a salt thereof can be obtained through at least the washing step in the above-mentioned production step.

As another embodiment of the present invention, in the long chain N-acyl acidic amino acid or a salt thereof, the content of the inorganic salts is not more than 1% by weight based on the weight of the long chain N-acyl acidic amino acid, and a content of the free fatty acid is not more than 3.0% by weight based on the weight of the long chain N-acyl acidic amino acid. The long chain N-acyl acidic amino acid or a salt thereof having a content of the free fatty acid of not more than 3.0% by weight based on the weight of long chain N-acyl acidic amino acid is unknown as far as the present inventors know. When the free fatty acid exceeds 3.0% by weight based on the weight of long chain N-acyl acidic amino acid, precipitation and turbidity occur at a low temperature when an aqueous solution of a salt of the long chain N-acyl acidic amino acid or a cosmetic composition prepared by incorporating a salt of the long chain N-acyl acidic amino acid into a liquid detergent. The content of the free fatty acid is preferably not more than 2.5% by weight, more preferably not more than 2.0% by weight. Such a long chain N-acyl acidic amino acid or a salt thereof can be obtained through at least the acylation reaction step, the washing step and the solvent distillation removal step in the above-mentioned production step.

As a further embodiment of the present invention, in the long chain N-acyl acidic amino acid or a salt thereof, the content of the inorganic salts is not more than 1% by weight based on the weight of the long chain N-acyl acidic amino acid, the content of tertiary butanol is from 0.1 to 750 ppm by weight based on the weight of the long chain N-acyl acidic amino acid, and the content of the free fatty acid is not more than 3.0% by weight based on the weight of the long chain N-acyl acidic amino acid. Such a long chain N-acyl acidic amino acid or a salt thereof can be obtained through at least the acylation reaction step, the washing step and the solvent distillation removal step in the above-mentioned production step.

The above-mentioned long chain N-acyl acidic amino acid in accordance with the present invention, wherein a content of impurities such as odoriferous substances originated from the hydrophilic organic solvent, the inorganic salts and the free fatty acid is limited to a fixed degree or less, can exhibit a remarkably superior performance when compared to a conventional one.

With respect to typical uses of the long chain N-acyl acidic amino acid, for example, there are enumerated materials for industrial detergent and treatment agent, materials for household (clothes, kitchen and house) detergent and materials for cosmetic products. It can be said that the uses as materials for cosmetic products are particularly effective, because such uses make the best use of low irritating property, which is a characteristic feature of the long chain N-acyl acidic amino acid or its salt.

The cosmetic products in the present invention are generically quasi-drugs and cosmetics described in Pharmaceutical Affairs Law. Specific examples of the quasi-drugs are refrigerant troches, underarm deodorants, baby powders, hair tonics, depilatory agents, hair dyes, permanent wave products, bath products, medicated cosmetics and medicated toothpastes or powders. Specific examples of the cosmetics are wash cosmetics such as toilet soap, face wash (cream; paste form, liquid; gel form, granule; powder form, aerosol), shampoo and hair rinse, hair cosmetics such as hair dye, hair treatment agent (cream form, mist form, oil form, gel form and other forms, and split hair coating agents), hair set agent (hair oil, set lotion, curler lotion, pomade, stick pomade, bintuke (sidelocks) oil, hair spray, hair mist, hair liquid, hair foam, hair gel, water grease), foundation cosmetics such as general cream, milky lotion (cleansing cream, cold cream, vanishing cream, hand cream), mustache shaving cream (after-shaving cream, shaving cream), toilet water (hand lotion, general lotion), Eau de Cologne, mustache shaving lotion (after-shaving lotion, shaving lotion), cosmetic oil and pack, makeup cosmetics such as toilet powder (cream powder, solid powder, face powder, talcum powder, paste powder, baby powder, body powder and liquid face-paint), powder, foundation (cream form, liquid form and solid), lipstick, eye-brow pencil, eye-cream and eye-shadow mascara, perfumery such as general perfume, paste perfume and powder perfume, sunburn or sunscreen cosmetics such as sunburn or sunscreen cream, sunburn or sunscreen lotion and sunburn or sunscreen oil, nail cosmetics such as nail cream, enamel and enamel remover, eye liner cosmetics, lip cosmetics such as lipstick and lip cream, oral cosmetics such as toothpaste or powder, and bath cosmetics such as bath salt and bath oil. Especially, the product of the present invention is extensively used for the above-mentioned wash cosmetics, hair cosmetics and foundation cosmetics, and in particular most suitably used in the wash cosmetics.

In addition, the product of the present invention can be used in combination with various kinds of materials usually used in cosmetic goods. Specific examples thereof are anionic surface active agents such as fatty acid salt (soap), alkyl sulfate (AS), polyoxyethylene alkyl ether sulfate (AES), α-olefin sulfonate (AOS), alkylbenzene sulfonate, alkylnaphthalene sulfonate, alkyl sulfonate (SAS), dialkyl sulfosuccinate, α-sulfonated fatty acid salt, N-acylaminate, salt of N-acyl-N-methyltaurine, sulfated fatty acid, polyoxyethylene styrene-modified phenyl ether sulfate, alkylphosphate, polyoxyethylene alkyl ether phosphate, polyoxyethylene alkylphenyl ether phosphate and formalin condensate of naphthalenesulfonate, amphoteric surface active agents such as alkylbetaine, alkylamidobetaine, alkylsulfobetaine and imidazolynium betaine, nonionic surface active agents such as fatty acid alkylolamide, alkylamine oxide, polyoxyethylene alkyl ether (AE), polyoxyethylene alkylphenyl ether, polyoxyethylene polystyrylpheny ether, polyoxyethylene polyoxypropylene glycol, polyoxyethylene polyoxypropylenealkyl ether, polyhydric alcohol fatty acid partial ester, polyoxyethylene polyhydric alcohol fatty acid partial ester, polyoxyethylene fatty acid ester, polyglycerol fatty acid ester, polyoxyethylene hardened caster oil, polyoxyethylene alkylamine and triethanolamine fatty acid partial ester, cationic surface active agents such as primary to tertiary aliphatic amine salt, alkyl chloride ammonium salt, tetraalkyl ammonium salt, trialkylbenzyl ammonium salt, alkylpyridinium salt, alkylhydroxyethylimidazolynium salt and dialkylmorpholinium salt, high molecular weight surface active agents such as sodium alginate, starch derivative and tragacanth gum, natural surface active agents such as lecithin, lanolin, cholesterol and saponin, fats and oils such as avocado oil, almond oil, olive oil, cacao oil, sesame oil, safflower oil, soybean oil, tsubaki oil, persic oil, caster oil, mink oil, cotton seed oil, Japan tallow, coconut oil, egg yolk oil, palm oil, palm kernel oil and synthetic triglyceride, hydrocarbons such as liquid paraffin, vaseline, ceresine, micro-crystalline wax and isoparaffin, wax such as beeswax, whale wax, hydrous lanolin, carnauba wax, candelilla wax and its derivative, higher fatty acids such as lauric acid, myristic acid, palmitic acid, stearic acid, isostearic acid, oleic acid, behenic acid, undecylenic acid, lanolin fatty acid, hard lanolin fatty acid and soft lanolin fatty acid, higher alcohols such as lauryl alcohol, cetanol, cetostearic alcohol, stearyl alcohol, oleyl alcohol, behenyl alcohol, lanolin alcohol, hydrogenated lanolin alcohol, hexyldecanol and octyldodecanol, ester oils such as isopropyl myristate and butyl stearate, volatile and nonvolatile oils such as metal soap and silicones including straight silicone oil and modified silicone oil, humectants such as polyols including glycerol, 1,3-butanediol, propanediol and polyethylene glycol, trimethylglycine, sorbitol, pyrrolidone carbonates, lactates and hyaluronates, water soluble and oil soluble polymers such as hydroxyethyl cellulose, carboxymethyl cellulose, hydroxyethyl cellulose hydroxypropyltrimethylammonium chloride ether, methyl cellulose, ethyl cellulose, hydroxypropyl cellulose, methyl hydroxypropyl cellulose, soluble starch, carboxymethyl starch, methyl starch, propylene glycol aluginate, polyvinyl alcohol, polyvinyl pyrrolidone, polyvinyl methyl ether, carboxyvinyl polymer, polyacrylate, guar gum, locust bean gum, quince seed, carrageenan, galactan, gum arabic, pectin, mannan, starch, xanthane gum, dextran, succinoglucan, curdlan, hyaluronic acid, gelatin, casein, albumin, collagen, methoxyethylene maleic anhydride copolymer, amphoteric methacrylate copolymer, polydimethyl chloride methylenepiperidium, polyacrylate copolymer, polyvinyl acetate, nitrocellulose and silicone resin, thickeners and frothers such as polyethylene glycol fatty acid ester, polyoxyethylene fatty acid ester methylglycoxide and tetradecene sulfonate, sequestering agents such as ethylenediaminetetraacetic acid and its salt, hydroxyethylenediaminetriacetic acid and its salt, phosphoric acid, ascorbic acid, succinic acid, gluconic acid, polyphosphate and metaphosphate, antiseptics such as paraoxybenzoate, benzoic acid and its salt and phenoxyethanol, buffer agents such as citric acid, malic acid, adipic acid, glutamic acid and aspartic acid, dandruff and itch removers such as trichlorocarbanide, salicylic acid, zinc pyrithion and isopropylmethylphenol, ultraviolet ray absorbers such as benzophenone derivative, p-aminobenzoic acid derivative, p-aminocinnamic acid derivative and salicylic acid derivative, whitening agents such as arbutin, kojic acid, ascorbic acid and derivatives thereof, blood circulation facilitating agents such as Japanese chirata extract, cepharanthine, vitamin E and its derivative and γ-oryzanol, local stimuli such as tincture of Japanese chillies, tincture of ginger, tincture of cantharis and benzyl nicotinate, eutrophy agents such as various vitamins and amino acids, female hormone drugs, hair bulb activators, anti-inflammatory agents such as glycyrrhetinic acid, glycyrrhetenic acid derivatives, allantoin, azulene, aminocaproic acid and hydrocortisone, astringents such as zinc oxide, zinc sulfate, allantoin hydroxy aluminum, aluminum chloride, zinc sulfophenoxide and tannic acid, cooling agents such as menthol and camphor, antihistamines, silicone substances such as high molecular silicone and cyclic silicone, tocopherols, antioxidants such as BHA, BHT, gallic acid and NDGA, and purified water.

Particularly, the combination use with fatty acid diethanolamide, polyoxyethylene dioleic acid methylglucoxide, distearic acid polyethylene glycol, tetradecene sulfonate, myristates and myristyldimethylamine is useful from a viewpoint of increasing viscosity and foaming power, and the combination use with each amphoteric surface active agent is remarkably useful from a viewpoint of further lessening the irritative property.

The present invention is illustrated in more detail with reference to Examples and others, but the present invention is by no means limited thereto.

Analysis means and the like used in Examples of the present invention and others are as follows.

(a) Determination of Inorganic Salt

Respective ions were measured using an inductively coupled plasma emission analysis apparatus, IRIS/AP (manufactured by Thermo Jarrell Ash), provided that a chlorine ion was ion-chromatographically measured under conditions of a column of DIONEX AS4SC, a guard column of AG4ASC, a suppressor of AMMS, an eluent of a mixed solution of 3 mmol/L $Na_2CO_3$ and 1 mmol/L $NaHCO_3$, and a regenerant of 0.05N $H_2SO_4$.

In the Examples, the content of the inorganic salts is expressed in terms of a numerical value based on the weight of the long chain N-acyl acidic amino acid.

(b) Determination of Long Chain N-acyl Acidic Amino Acid and Free Fatty Acid

This was determined according to high speed liquid chromatography (HPLC) using an ODS column, an eluent of methanol/water/phosphoric acid, an ultraviolet detector and a differential refractometric detector.

In the Examples, all of the free fatty acid contents were expressed in terms of % by weight based on the weight of long chain N-acyl acidic amino acid.

(c) Determination of Solid Content

Solid content was measured according to weight loss on drying at 105° C. for 3 hours. The solid content is defined as follows.

Solid content (% by weight)=weight after drying/weight before drying×100

(d) Determination of Tertiary Butanol

Tertiary butanol was determined using a gas chromatograph (GC-14A, manufactured by Shimadzu Corporation), a hydrogen flame ionization detector, and a glass column of a 3 mm inner diameter, which was packed with a liquid phase of PEG20M 20% and a carrier of 60 to 80 mesh ChromosorbW AW-DMCS, in a manner such that at an injection temperature of 200° C., a column temperature was held at 120° C. for 0 to 10 minutes, thereafter raised to 200° C. at 30° C./min and held at 200° C. for 15 minutes.

The tertiary butanol content in Examples is based on the weight of the long chain N-acyl acidic amino acid.

(e) Organoleptic Odor Test

An evaluation of an odor was carried out by 4 men and 1 woman, who were all healthy, with respect to an aqueous solution of a salt of a long chain N-acyl acidic amino acid or a shampoo composition prepared by using said aqueous solution of a salt of a long chain N-acyl acidic amino acid. In evaluating, the liquid to be tested was placed in a glass screw pipe (35 mm diameter×78 mm height) and the temperature thereof was held at room temperature and 80° C., respectively. In the evaluation results of Examples, the case where nobody was aware of any odor such as an odor of fatty acid or that of tertiary butanol is marked with ○ the case where any only one person among fives was aware of such an odor is marked with X (f) Evaluation of Low Temperature Stability An aqueous solution of a triethanolamine salt having a solid content of 30% by weight in an amount of 10 ml was allowed to cool to a temperature of not higher than −18° C., and the temperature of either turbidity or white precipitation (solidifying point) was observed.

The case where neither turbidity nor precipitation was observed even when the liquid temperature reached −10° C. is marked with ○, and the case where either turbidity or precipitation was observed when the liquid temperature reached −10° C. or higher is marked with X.

The result of this test is highly correlative to a low temperature stability of a cosmetic composition prepared by incorporating the material into a liquid detergent or the like.

(g) Evaluation of Low Temperature Stability of Shampoo Composition

A shampoo composition was prepared according to the blending compositions shown in Table 2, and held at 5° C. The occurrence of turbidity was observed at 1 day, 1 week, 1 month, 3 months, and 6 months, respectively.

The present invention is illustrated in detail in the Examples but is not limited by the examples.

(h) Determination of Carboxyl Group Content

About 0.3 g of a sample was accurately weighed and dissolved in ethanol/water, and a phenolphthalein indicator was added thereto, followed by titration with an ethanolic potassium hydroxide solution.

REFERENCE EXAMPLES 1 TO 7

The separation region in the mixed system of long chain N-acyl acidic amino acid/tertiary butanol/water, which is the principle of purification of the long chain N-acyl acidic amino acid in the washing step of the present invention, was measured by varying the mixing ratio of the abovementioned components as are shown in Table 1. Data of respective compositions relating to an organic layer and an aqueous layer separated from the system of N-cocoyl-L-glutamic acid/tertiary butanol/water are shown. The temperature was 40° C.

REFERENCE EXAMPLES 8 AND 9

The data of Table 1 was taken in a manner similar to that of Reference Examples 1 to 7, as an example to show a separation region in the mixed system of long chain N-acyl acidic amino acid/tertiary butanol/water in the washing step. Data of respective compositions relating to an organic layer and an aqueous layer separated from the system of N-cocoyl-L-glutamic acid/tertiary butanol/water are shown. The temperature was 65° C.

EXAMPLE 1

Acylation Step

To a mixed solution of 1,444 g (7.72 mol) of monosodium L-glutamate monohydrate, 3,070 g of pure water and 1,235 g of 25% by weight sodium hydroxide aqueous solution (sodium hydroxide 7.72 mol), 1647 ml of 88% by volume tertiary butanol aqueous solution was added, and 1,760 g (7.56 mol, free fatty acid content 2% by weight) of cocoyl chloride was dropwise added under a stirring power of 0.5 kW/m$^3$ over 2.5 hours, while cooling the resulting solution and adjusting to pH 12 with use of 25% by weight sodium hydroxide.

Acid-precipitation Separation Step

Stirring was further continued for 30 minutes, and thereafter the pH of the liquid was adjusted to 2 by dropwise adding 75% sulfuric acid, and the temperature was kept at 65° C. After completion of the dropwise addition, stirring was finished, and the liquid was allowed to stand at 65° C. for 20 minutes, thereby separating into an organic layer and an aqueous layer. The organic layer was obtained. A composition of the organic layer obtained is shown in Table 2.

Washing Step

Washing One Time

To the separated organic layer, tertiary butanol and water were added to obtain a mixed liquid of N-cocoyl-L-glutamic acid/tertiary butanol/water in a proportion of 33/25/42(% by weight, respectively), and the mixed liquid was stirred at 65° C. for 20 minutes. After finishing the stirring, the mixed liquid was allowed to stand at 65° C. for 20 minutes, thereby separating into an organic layer and an aqueous layer. A composition of the organic layer obtained therefrom and a content of the remaining inorganic salt are shown in Table 2.

Solvent Distillation Removal Step

Triethanolamine was added to the organic layer separated and obtained so as to convert 50% of the carboxyl group of the N-cocoyl-L-glutamic acid in the organic layer to its salt, and purified water was added thereto so as to make a solid content of 30% by weight. The resulting liquid was mixed under stirring.

Thereafter, using a 10 L glass vessel, vacuum distillation was conducted under a pressure of 327 mmHg, while adding purified water to maintain a solid content to 30% by weight. 12 Hours after starting the distillation, the liquid temperature reached 78° C., and then the distillation was finished, thereby obtaining an aqueous solution of triethanolamine N-cocoyl-L-glutamate. The aqueous solution was found to have a solid content of 30% by weight, an N-cocoyl-L-glutamic acid yield of 96.5% (in terms of acid), a tertiary butanol concentration of 60 ppm by weight, and a free acid content of 2.3% by weight.

The results are summarized in Table 2 and Table 3.

EXAMPLE 2

Example 1 was repeated, except that the temperature and standing time in the acid-precipitation step were changed to 50° C. and 25 minutes, respectively, and the temperature and standing time in the washing step were changed to 50° C. and 30 minutes, respectively. After the separation, an organic layer was obtained through a further separation.

Further, after adding potassium hydroxide to the organic layer obtained through a further separation so as to convert 75% of the carboxyl group of the N-cocoyl-L-glutamic acid in the organic layer to its salt, and further adding pure water thereto so as to make a solid content 30% by weight, the resulting liquid was mixed by stirring. Thereafter, the solvent distillation removal step was conducted under conditions shown in Table 2.

Twelve hours after starting the distillation, the liquid temperature reached 52° C., and then the distillation was finished to obtain an aqueous solution of potassium N-cocoyl-L-glutamate.

The results are summarized in Table 2 and Table 3.

EXAMPLE 3

Example 1 was repeated up to the washing step to obtain an organic layer. To the separated organic layer, tertiary butanol and water were added to obtain a mixed liquid of N-cocoyl-L-glutamic acid/tertiary butanol/water in a proportion of 29/18/53(% by weight, respectively), and the mixed liquid was stirred at 65° C. for 20 minutes. After finishing the stirring, the mixed liquid was allowed to stand at 65° C. for 20 minutes, thereby separating into an organic layer and an aqueous layer. After said separation, the organic layer was obtained through a further separation.

After adding 25% sodium hydroxide aqueous solution to the organic layer obtained through a further separation so as to convert 75% of the carboxyl group of the N-cocoyl-L-glutamic acid in the organic layer to its salt, and further adding pure water thereto so as to make a solid content 25% by weight, the resulting liquid was mixed under stirring. Thereafter, the solvent distillation removal step was conducted under conditions as shown in Table 2.

Twelve hours after starting the distillation, the liquid temperature reached 68° C., and then the distillation was finished to obtain an aqueous solution of sodium N-cocoyl-L-glutamate.

The results are summarized in Table 2 and Table 3.

EXAMPLE 4

Example 3 was repeated up to the washing, except that the washing step was conducted two times, thereby obtaining an organic layer. To the separated organic layer, tertiary butanol and water were added to obtain a mixed liquid of N-cocoyl-L-glutamic acid/tertiary butanol/water in a proportion of 19/27/54(% by weight, respectively), and the mixed liquid was stirred at 65° C. for 20 minutes. After finishing the stirring, the mixed liquid was allowed to stand at 65° C. for 20 minutes, thereby separating into an organic layer and an aqueous layer. After said separation, the organic layer was obtained through a further separation.

To the organic layer obtained through a further separation, triethanolamine was added so as to convert 50% of the carboxyl group of the N-cocoyl-L-glutamic acid in the organic layer to its salt, and further pure water was added thereto so as to make a solid content 30% by weight. The resulting liquid was mixed under stirring.

Thereafter, using a spray evaporator, the neutralization solvent distillation removal step was conducted.

Figure 2:
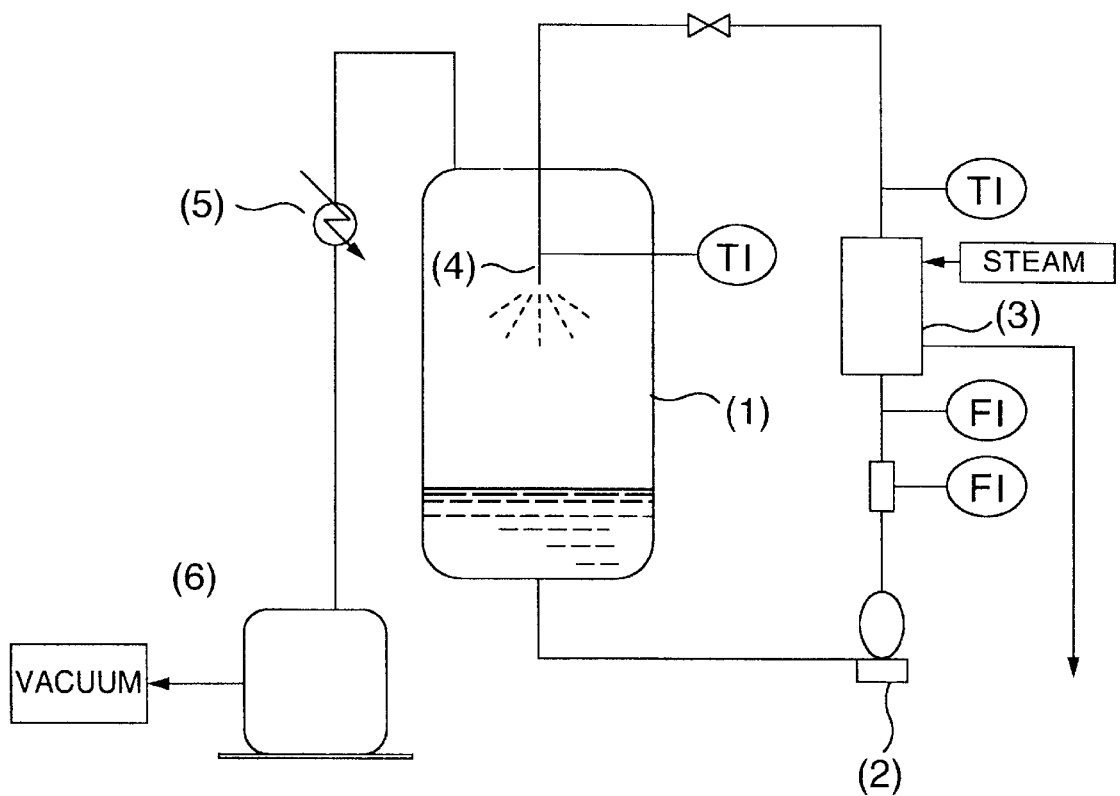
FIG. 2 is to show a schematic view of a spray-evaporating apparatus.

A spray evaporating apparatus is shown in FIG. 2. The apparatus is composed of (1) evaporation can (inner diameter 300 mm, height 700 mm), (2) liquid-circulating pump, (3) heat exchanger, (4) nozzle (inner diameter of a line end 4 mm) for spraying a heated vapor-liquid mixed-phase flow into the evaporation can, (5) condenser for condensing evaporated gas, and (6) tank of distilled liquid. In FIG. 2, TI and FI stand for a temperature indicator and flow indicator, respectively.

The operation of the apparatus is generally explained. The liquid is circulated from the lower part of the evaporator with the pump, and sent to the heat exchanger. The liquid going out of the heat exchanger is superheated, and coming near the nozzle end, gradually evaporates to form a vapor-liquid mixed-phase. It is noted that the distillation can be carried out under a non-bubble condition even when a liquid capable of bubbling is used, when a flow rate of the circulated liquid (a linear velocity at the nozzle end) and a degree of excess heat (difference between a temperature of the liquid entering into the heat exchanger and that of the liquid going out of the heat exchanger) are controlled so as to make an intermittent flow as the flow form at this time.

In the present Example, vacuum distillation was conducted under conditions of pressure of 163 mmHg, a linear velocity of the liquid at the nozzle end of about 1.5 m/sec, and a liquid excess heat of about 20° C., while adding pure water so as to keep a solid content of 30% by weight at the time of distillation. 3.5 Hour-after starting the distillation, the liquid temperature reached 62° C., and then the distillation was finished to obtain an aqueous solution of triethanolamine N-cocoyl-L-glutamate.

The results are summarized in Table 2 and Table 3.

EXAMPLE 5

Example 3 was repeated up to the washing step, except that the washing step was conducted two times. To the organic layer obtained through a further separation, potassium hydroxide was added so as to convert 75% of the carboxyl group of the N-cocoyl-L-glutamic acid in the organic layer to its salt, and pure water was added thereto so as to make a solid content of 28% by weight. The resulting liquid was mixed under stirring. Thereafter, the neutralization solvent distillation removal step was carried out as follows. Using the same apparatus as in Example 4, the operation of Example 4 was repeated, except that the pressure condition was changed to 83 mmHg. 3.5 Hours after starting the distillation, the liquid temperature reached 46° C., and then the distillation was finished to obtain an aqueous solution of potassium N-cocoyl-L-glutamate.

The results are summarized in Table 2 and Table 3.

EXAMPLE 6

Example 3 was repeated up to the washing step, except that the washing step was conducted two times. To the organic layer obtained through a further separation, 25% sodium hydroxide aqueous solution was added so as to convert 75% of the carboxyl group of the N-cocoyl-L-glutamic acid in the organic layer to its salt, and further pure water was added thereto so as to make a solid content of 25% by weight. The resulting liquid was mixed under stirring. Thereafter, the neutralization solvent distillation removal step was carried out as follows.

Using the same apparatus as in Example 4, the operation of Example 4 was repeated, except that the pressure condition was changed to 254 mmHg. 3.5 Hours after starting the distillation, the liquid temperature reached 72° C., and then the distillation was finished to obtain an aqueous solution of sodium N-cocoyl-L-glutamate.

The results are summarized in Table 2 and Table 3.

EXAMPLE 7

Example 1 was repeated up to the washing step, except that cocoyl chloride was replaced by lauroyl chloride. To the organic layer obtained through a further separation, triethanolamine was added so as to convert 50% of the carboxyl group of the N-lauroyl-L-glutamic acid in the organic layer to its salt, and pure water was added thereto so as to make a solid content of 30% by weight. The resulting liquid was mixed under stirring. Thereafter, the neutralization solvent distillation removal step was carried out as follows.

Using the same apparatus as in Example 4, the operation of Example 4 was repeated, except that the pressure condition was changed to 149 mmHg. Four hours after starting the distillation, the liquid temperature reached 60° C., and then the distillation was finished to obtain an aqueous solution of triethanolamine N-lauroyl-L-glutamate.

The results are summarized in Table 2 and Table 3.

EXAMPLE 8

Example 3 was repeated up to the washing step, except that the washing step was conducted two times, and thereafter the solvent distillation removal step was conducted as follows.

Using the same apparatus as in Example 4, the operation of Example 4 was repeated, except that the inner diameter of the line end in the spray nozzle of the spray evaporating apparatus was changed to 10 mm, and the pressure condition was changed to 265 mmHg.

Two hours after starting the distillation, the liquid was sampled, and a weight ratio between N-cocoyl-L-glutamic acid and water and a tertiary butanol concentration in the liquid were found to be 55/45 and 4.2% by weight(in-liquid concentration), respectively, and at that time, the liquid temperature was 68° C. Further, four hours after starting the distillation, a weight ratio between N-cocoyl-L-glutamic acid and water and a tertiary butanol concentration in the liquid were found to be 53/47 and 5 ppm by weight(in-liquid concentration), respectively, and at that time, the liquid temperature reached 73° C. Then, the distillation was finished to obtain a mixed liquid containing 53% by weight of N-cocoyl-L-glutamic acid. The mixed liquid was dried to obtain a white solid of N-cocoyl-L-glutamic acid.

The results are summarized in Table 2 and Table 3.

EXAMPLE 9

Example 3 was repeated up to the washing step, and thereafter the solvent distillation removal step was conducted as follows.

Using the same apparatus as in Example 4, the operation of Example 4 was repeated, except that the inner diameter of line end in the spray nozzle of the spray evaporating apparatus was changed to 10 mm, and the pressure condition was changed to 356 mmHg. Two hours after starting the distillation, the liquid was sampled, and a weight ratio between N-cocoyl-L-glutamic acid and water and a tertiary butanol concentration in the liquid were found to be 40/60 and 2.0% by weight(in-liquid concentration), respectively, and at that time, the liquid temperature was 75° C. Four hours after starting the distillation, a weight ratio between N-cocoyl-L-glutamic acid and water and a tertiary butanol concentration in the liquid were found to be 41/59 and 6 ppm by weight(in-liquid concentration), respectively, and at that time, the liquid temperature reached 80° C. Then, the distillation was finished to obtain a mixed liquid containing 41% by weight of N-cocoyl-L-glutamic acid. The mixed liquid was dried to obtain a white solid of N-cocoyl-L-glutamic acid.

The results are summarized in Table 2 and Table 3.

EXAMPLE 10

Example 3 was repeated up to the washing step, and thereafter the solvent distillation removal step was conducted as follows.

Using the same apparatus as in Example 4, the operation of Example 4 was repeated, except that the inner diameter of the line end in the spray nozzle of the spray evaporating apparatus was changed to 10 mm, and the pressure condition was changed to 468 mmHg. Two hours after starting the distillation, the liquid was sampled, and a weight ratio between N-cocoyl-L-glutamic acid and water and a tertiary butanol concentration in the liquid were found to be 60/40 and 2.5% by weight (in liquid concentration), respectively, and at that time, the liquid temperature was 81° C. Four hours after starting the distillation, the weight ratio between N-cocoyl-L-glutamic acid and water and a tertiary butanol concentration in the liquid were found to be 62/38 and 6 ppm by weight (in-liquid concentration), respectively, and at that time, the liquid temperature reached 87° C. Then, the distillation was finished to obtain a mixed liquid containing 62% by weight of N-cocoyl-L-glutamic acid. The mixed liquid was dried to obtain a white solid of N-cocoyl-L-glutamic acid.

The results are summarized in Table 2 and Table 3.

EXAMPLE 11

Example 1 was repeated up to the washing step, except that cocoyl chloride in the acylation reaction step was changed to lauroyl chloride, and the temperature in the washing step was changed to 50° C. Thereafter, the solvent distillation removal step was conducted as follows.

Using the same apparatus as in Example 4, the operation of Example 4 was repeated, except that the inner diameter of line end in the spray nozzle of the spray evaporating apparatus was changed to 10 mm, and the pressure condition was changed to 234 mmHg. Two hours after starting the distillation, the liquid was sampled, and a weight ratio between N-lauroyl-L-glutamic acid and water and a tertiary butanol concentration in the liquid were found to be 51/49 and 3.5% by weight(in-liquid concentration), respectively, and at that time, the liquid temperature was 64° C. Four hours after starting the distillation, a weight ratio between N-lauroyl-L-glutamic acid and water and a tertiary butanol concentration in the liquid were found to be 50/50 and 5 ppm by weight(in-liquid concentration), respectively, and at that time, the liquid temperature reached 70° C. Then, the distillation was finished to obtain a mixed liquid containing 50% by weight of N-lauroyl-L-glutamic acid. The mixed liquid was dried to obtain a white solid of N-lauroyl-L-glutamic acid.

The results are summarized in Table 2 and Table 3.

EXAMPLE 12

Example 1 was repeated up to the washing step, except that sodium L-glutamate monohydrate and its amount in the acylation reaction step were changed to L-aspartic acid and 1028 g (7.72 mol), and the temperatures in the acid-precipitation separation step and the washing step were changed to 50° C., respectively. Thereafter the solvent distillation removal step was conducted as follows.

Using the same apparatus as in Example 4, the operation of Example 4 was repeated, except that the inner diameter of the line end in the spray nozzle of the spray evaporating apparatus was changed to 10 mm, and the pressure condition was changed to 265 mmHg.

The solvent distillation removal step was carried out as follows.

Two hours after starting the distillation, the liquid was sampled, and a weight ratio between N-cocoyl-L-aspartic acid and water and a tertiary butanol concentration in the liquid were found to be 54/46 and 3.6% by weight(in-liquid concentration), respectively, and at that time, the liquid temperature was 69° C. Further, four hours after starting the distillation, a weight ratio between N-cocoyl-L-aspartic acid and water and a tertiary butanol concentration in the liquid were found to be 54/46 and 10 ppm by weight(in-liquid concentration), respectively, and at that time, the liquid temperature reached 73° C. Then, the distillation was finished to obtain a mixed liquid containing 54% by weight of N-cocoyl-L-aspartic acid. The mixed liquid was dried to obtain a white solid of N-cocoyl-L-aspartic acid.

The results are summarized in Table 2 and Table 3.

EXAMPLE 13

An acylation reaction step was carried out in the same manner as in Example 1, except that tertiary butanol and the amount of pure water in the acylation reaction step in Example 1 were changed to acetone, and 2,405 g, respectively, and acetone was used in an amount of 2,312 ml. To the resulting reaction mixture, 20 L of water was added, and 75% sulfuric acid was added thereto to adjust the liquid to pH 1. The crude crystal of N-cocoyl-L-glutamic acid precipitated was separated by filtration and dried. The obtained N-cocoyl-L-glutamic acid was found to contain sodium chloride and sodium sulfate as the inorganic salts in amounts of 1.7% by weight and 1.2% by weight, respectively, based on the weight of N-cocoyl-L-glutamic acid. In addition, the odor that originated from acetone condensation products was severe. Further, the obtained N-cocoyl-L-glutamic acid was adjusted to the same mixed liquid composition as in the washing step of Example 1, that is N-cocoyl-L-glutamic acid/tertiary butanol/water=33/25/42 (% by weight, respectively). The resulting liquid was stirred at 65° C. for 20 minutes, and then allowed to stand at 65° C. for 20 minutes, thereby separating into an organic layer and an aqueous layer.

Thereafter, using the resulting mixed liquid, the solvent distillation removal step was carried out as follows.

Using the same apparatus as in Example 4, the operation of Example 4 was repeated, except that the inner diameter of the line end in the spray nozzle of the spray evaporating apparatus was changed to 10 mm, and the pressure condition was changed to 265 mmHg. Two hours after starting the distillation, the liquid was sampled, and a weight ratio between N-cocoyl-L-glutamic acid and water and a tertiary butanol concentration in the liquid were found to be 53/47 and 4.1% by weight (in liquid concentration), respectively, and at that time, the liquid temperature was 68° C. Four hours after starting the distillation, the weight ratio between N-cocoyl-L-glutamic acid and water and a tertiary butanol concentration in the liquid were found to be 53/47 and 5 ppm by weight (in-liquid concentration), respectively, and at that time, the liquid temperature reached 73° C. Then, the distillation was finished to obtain a mixed liquid containing 53% by weight of N-cocoyl-L-glutamic acid. The mixed liquid was dried to obtain a white solid of N-cocoyl-L-glutamic acid. The obtained crystal had almost no odor that originated from the acetone condensation products.

The results are summarized in Table 2 and Table 3.

COMPARATIVE EXAMPLE 1

Example 1 was repeated up to the acid-precipitation step, except that the amount of cocoyl chloride was changed to 1,976 g (8.49 mol). To the obtained organic layer, tertiary butanol and water were added to obtain a mixed liquid having a composition of N-cocoyl-L-glutamic acid/tertiary butanol/water=28/58/14 (% by weight, respectively). The mixed liquid was stirred at 65° C. for 20 minutes. After finishing the stirring, the mixed liquid was allowed to stand at 65° C. for 60 minutes, but no separation of the liquid was found.

The mixed liquid was subjected to solvent distillation removal under the same conditions as those in the solvent distillation removal step of Example 1. 12 Hours after starting the distillation, the liquid temperature reached 78° C., and then the distillation was finished, thereby obtaining an aqueous solution of triethanolamine N-cocoyl-L- glutamate. The product was found to contain the free fatty acid and inorganic salts in each large amount.

The results are summarized in Table 2 and Table 3.

COMPARATIVE EXAMPLE 2

Example 1 was repeated up to the acid-precipitation step, except that tertiary butanol and the amount of pure water in the acylation reaction step were changed to acetone and 2,405 g, respectively, acetone was used in an amount of 2,312 ml, and the temperature in the acid-precipitation separation step was changed to 50° C. To the obtained organic layer, acetone and water were added to obtain a mixed liquid having a composition of N-cocoyl-L-glutamic acid/acetone/water=33/25/42 (% by weight, respectively). The mixed liquid was stirred at 50° C. for 20 minutes, and thereafter allowed to stand for 60 minutes, but no separation of the liquid was found.

The mixed liquid was subjected to solvent distillation removal under conditions similar to those in the solvent distillation removal step of Example 1, except that pressure was changed to atmospheric pressure. 15 Hour-after starting the distillation, the liquid temperature reached 100° C., and then the distillation was finished, thereby obtaining an aqueous solution of triethanolamine N-cocoyl-L-glutamate having a solid content of 30% by weight. The product was found to contain the free fatty acid and inorganic salts in each large amount, and there was aware of an odor originated from the acetone condensation products.

The results are summarized in Table 2 and Table 3.

COMPARATIVE EXAMPLE 3

Example 1 was repeated up to the acid-precipitation step. To the resulting organic layer, a 25% sodium hydroxide aqueous solution was added so as to convert 75% of the carboxyl group of N-cocoyl-L-glutamic acid to its salt, and pure water was added thereto so as to make a solid content of 25% by weight. The resulting mixed liquid was treated in the same manner as in Example 1, except that the solvent distillation removal step was carried out as follows.

Vacuum distillation was conducted under pressure of 187 mmHg without addition of pure water.

As the concentration proceeded, the liquid increased its viscosity and resulted in solidification in a gel form, and therefore the distillation was discontinued. At this time, a solid concentration was found to be 55% by weight, and tertiary butanol remained in an amount of 5% by weight based on the weight of N-cocoyl-L-glutamic acid.

The results are summarized in Table 2 and Table 3.

COMPARATIVE EXAMPLE 4

Example 1 was repeated up to the acid-precipitation separation step. Using a 10 L glass vessel, the obtained organic layer was heated under vacuum to distillation-remove tertiary butanol and water, during which no water was added. On the way, the liquid bubbled, and therefore the distillation was continued while controlling the pressure within a range of from 40 mmHg to atmospheric pressure. 15 Hour-after starting the distillation, the temperature reached 105° C. and then the distillation was finished.

To the resulting liquid, triethanolamine was added so as to convert 50% of the carboxyl group of N-cocoyl-L-glutamic acid to its salt, and further pure water was added thereto so as to make a solid content 30% by weight. The liquid was mixed under stirring to obtain an aqueous solution of triethanolamine N-cocoyl-L-glutamate. A yield (as acid) of N-cocoyl-L-glutamic acid, a tertiary butanol concentration and a free fatty acid content were found to be 92.3%, 80 ppm by weight and 6.5% by weight, respectively.

The results are summarized in Table 2 and Table 3.

COMPARATIVE EXAMPLE 5

Example 1 was repeated up to the acid-precipitation separation step, except that cocoyl chloride was changed to lauroyl chloride. Using a 10 L glass vessel, the obtained organic layer was heated under vacuum to distillation-remove tertiary butanol and water, during which no water was added. During distillation, the liquid bubbled, and therefore the distillation was continued while controlling the pressure within a range of from 40 mmHg to atmospheric pressure. Fifteen hours after starting the distillation, the temperature reached 110° C., and then the distillation was finished.

To the resulting liquid, triethanolamine was added so as to convert 50% of the carboxyl group of N-lauroyl-L-glutamic acid to its salt, and further pure water was added thereto so as to make a solid content 30% by weight. The liquid was mixed under stirring to obtain an aqueous solution of triethanolamine N-lauroyl-L-glutamate. A yield (as acid) of N-lauroyl-L-glutamic acid, a tertiary butanol concentration and a free fatty acid content were found to be 90.5%, 60 ppm by weight and 8.3% by weight, respectively.

The results are summarized in Table 2 and Table 3.

COMPARATIVE EXAMPLE 6

Example 1 was repeated up to the acid-precipitation separation step, thereby obtaining an organic layer through a further separation. The mixed liquid was subjected to solvent distillation removal under conditions similar to those in the solvent distillation removal step of Example 1, except that pressure was changed to 588 mmHg. Twelve hours after starting the distillation, the liquid temperature reached 93° C., and then the distillation was finished, thereby obtaining an aqueous solution of triethanolamine N-cocoyl-L-glutamate having a solid content of 30% by weight.

A yield (as acid) of N-cocoyl-L-glutamic acid, a tertiary butanol concentration and a free fatty acid content were found to be 95.3%, 60 ppm by weight and 3.5% by weight, respectively.

EXAMPLE 14

Using the aqueous solutions of long chain N-acyl acidic amino acid salts obtained in the above Examples and Comparative Examples, the organoleptic odor test mentioned in the above item (e) was carried out at room temperature and 80° C. Incidentally, with respect to the the N-cocoyl-L-glutamic acid and N-lauroyl-L-glutamic acid obtained in Examples 8 to 13, before using them, triethanolamine was added thereto to convert 50% of the carboxyl group to each salt, and further pure water was added thereto to make a solid content 30% by weight, thereby obtaining each aqueous solution of triethanolamine salt having a solid content of 30% by weight.

The results are also shown in Table 3.

EXAMPLE 15

Using the aqueous solutions of long chain N-acyl acidic amino acids obtained in Example 1, Example 4, Example 7, Comparative Example 1, Comparative Example 2, Comparative Example 4 and Comparative Example 5, the low temperature stability test of technical compound mentioned in the above item (f) was carried out. Further, using solutions obtained in Example 8, Example 10, Example 11 and Example 13, the same test was carried out, provided that before using them, triethanolamine was added thereto to convert 50% of the carboxyl group of long chain N-acyl acidic amino acid in the liquid to each salt, and further pure water was added thereto to make a solid content 30% by weight, thereby obtaining each aqueous solution of triethanolamine salt having a solid content of 30% by weight.

The results are shown in Table 4.

EXAMPLE 16

Using the material obtained in Example 1, Example 4, Comparative Example 2 and Comparative Example 6, each shampoo composite liquid having a composition as shown in Table 5 was prepared in the following manner.

Cationic cellulose was dissolved in a portion of purified water, while being heated. The remaining components were mixed in a separate portion at 80° C. to be made uniform. Both portions were combined and mixed to be made uniform, then cooled and filled in a vessel.

The thus obtained shampoo composite liquid was kept at 5° C., and one day thereafter, one week thereafter, one month thereafter, three months thereafter and six months thereafter, the occurrence of turbidity was observed.

As a result, each shampoo composite liquid containing the product of either Example 1 or Example 4 was found to be clear even six months thereafter. Whereas, in each shampoo composite liquid containing the product of either Comparative Example 2 or Comparative Example 6, a great turbidity was observed one day thereafter, so that properties essential to the shampoos were markedly impaired.

In addition, in using the shampoo composite liquids, the organoleptic odor test mentioned in the above item (e) was carried out at room temperature and 80° C.

As a result, the odor results relating to each shampoo composite liquid containing products of Example 1, Example 4 or Comparative Example 6 revealed ○ (no odor observed), and on the other hand, the result relating to Comparative Example 2 revealed X (one person in five observes an odor).

INDUSTRIAL APPLICABILITY

The process in accordance with the present invention is a simple process for producing a long chain N-acyl acidic amino acid, which can be put into practice with industrial stability. Further, the long chain N-acyl acidic amino acid or a salt thereof produced according to the present invention has substantially no odor, and when incorporated into a liquid detergent or a cosmetic composition, it is capable of giving a long chain N-acyl acidic amino acid-containing cosmetic composition, which causes neither turbidity nor precipitation even for long storage times particularly at low temperatures.

TABLE 1

| | Mixed liquid | | | Organic layer | | | Aqueous layer | | |
| --- | --- | --- | --- | --- | --- | --- | --- | --- | --- |
| Reference Example | Cocoyl glutamic acid wt % | TBA wt % | $H_2O$ wt % | Cocoyl glutamic acid wt % | TBA wt % | $H_2O$ wt % | Cocoyl glutamic acid wt % | TBA wt % | $H_2O$ wt % |
| 1 | 34 | 26 | 40 | 45 | 32 | 24 | 0.2 | 14 | 86 |
| 2 | 38 | 25 | 37 | 43 | 27 | 30 | 0.4 | 14 | 86 |
| 3 | 38 | 25 | 37 | 43 | 27 | 30 | 0.4 | 14 | 86 |
| 4 | 28 | 14 | 58 | 43 | 15 | 42 | 0.4 | 12 | 88 |
| 5 | 14 | 35 | 51 | 17 | 39 | 44 | 0.4 | 19 | 81 |
| 6 | 29 | 39 | 32 | 31 | 40 | 29 | 0.4 | 17 | 82 |
| 7 | 10 | 30 | 60 | 21 | 44 | 35 | 0.4 | 18 | 81 |
| 8 | 32 | 21 | 46 | 46 | 27 | 27 | 0.2 | 8 | 92 |
| 9 | 31 | 28 | 41 | 40 | 31 | 29 | 0.5 | 7 | 93 |

TABLE 2

| | Acylation step | | | | Acid-precipitation separation step | | |
| --- | --- | --- | --- | --- | --- | --- | --- |
| | | | | | Composition of organic layer after acid-precipitation | | |
| Example | Acidic amino acid | Fatty acid halide | Organic solvent | Temperature ° C. | Acyl amino acid wt % | TBA wt % | Water wt % |
| Example 1 | L-Glutamic acid | Cocoyl chloride | TBA | 65 | 62 | 24 | 14 |
| Example 2 | L-Glutamic acid | Cocoyl chloride | TBA | 50 | 50 | 37 | 13 |
| Example 3 | L-Glutamic acid | Cocoyl chloride | TBA | 65 | 62 | 24 | 14 |
| Example 4 | L-Glutamic acid | Cocoyl chloride | TBA | 65 | 62 | 24 | 14 |
| Example 5 | L-Glutamic acid | Cocoyl chloride | TBA | 65 | 62 | 24 | 14 |
| Example 6 | L-Glutamic acid | Cocoyl chloride | TBA | 65 | 62 | 24 | 14 |
| Example 7 | L-Glutamic acid | Lauroyl chloride | TBA | 65 | 62 | 24 | 14 |
| Example 8 | L-Glutamic acid | Cocoyl chloride | TBA | 65 | 62 | 24 | 14 |
| Example 9 | L-Glutamic acid | Cocoyl chloride | TBA | 65 | 62 | 24 | 14 |
| Example 10 | L-Glutamic acid | Cocoyl chloride | TBA | 65 | 62 | 24 | 14 |
| Example 11 | L-Glutamic acid | Lauroyl chloride | TBA | 50 | 51 | 39 | 10 |
| Example 12 | L-Aspartic acid | Lauroyl chloride | TBA | 50 | 52 | 37 | 11 |
| Example 13 | L-Glutamic acid | Cocoyl chloride | Acetone | | Crystallization and filtration were conducted | | |
| Comparative Example 1 | L-Glutamic acid | Cocoyl chloride | TBA | 65 | 62 | 24 | 14 |

TABLE 2-continued

| Example | | | | | | | |
|---|---|---|---|---|---|---|---|
| Comparative Example 2 | L-Glutamic acid | Cocoyl chloride | Acetone | 50 | 50 | Acetone 40 | 10 |
| Comparative Example 3 | L-Glutamic acid | Cocoyl chloride | TBA | 65 | 62 | 24 | 14 |
| Comparative Example 4 | L-Glutamic acid | Cocoyl chloride | TBA | 65 | 62 | 24 | 14 |
| Comparative Example 5 | L-Glutamic acid | Lauroyl chloride | TBA | 65 | 49 | 37 | 14 |
| Comparative Example 6 | L-Glutamic acid | Cocoyl chloride | TBA | 65 | 62 | 24 | 14 |

| | Washing step | | | | | | |
|---|---|---|---|---|---|---|---|
| | | Composition of mixed liquid after washing | | | Composition of organic layer after separation | | |
| Example | Temperature °C. | Acyl amino acid wt % | TBA wt % | Water wt % | Acyl amino acid wt % | TBA wt % | Water wt % |
| Example 1 | 65 | 31 | 22 | 47 | 45 | 28 | 27 |
| Example 2 | 65 | 32 | 22 | 46 | 45 | 27 | 28 |
| Example 3 | Two times 65 | 30 | 25 | 45 | 44 | 32 | 24 |
| Example 4 | Three times 65 | 19 | 27 | 54 | 34 | 35 | 31 |
| Example 5 | Two times 65 | 30 | 25 | 45 | 44 | 32 | 24 |
| Example 6 | Two times 65 | 30 | 25 | 45 | 44 | 32 | 24 |
| Example 7 | 65 | 31 | 22 | 47 | 45 | 28 | 27 |
| Example 8 | Two times 65 | 30 | 25 | 45 | 44 | 32 | 24 |
| Example 9 | Two times 65 | 30 | 25 | 45 | 44 | 32 | 24 |
| Example 10 | Two times 65 | 30 | 25 | 45 | 44 | 32 | 24 |
| Example 11 | 65 | 33 | 25 | 42 | 44 | 30 | 26 |
| Example 12 | 50 | 25 | 20 | 55 | 40 | 27 | 33 |
| Example 13 | 65 | 33 | 25 | 42 | 43 | 27 | 30 |
| Comparative Example 1 | 65 | 25 | 58 | 14 | No separation | | |
| Comparative Example 2 | 50 | 33 | Acetone 25 | 42 | No separation | | |
| Comparative Example 3 | No conducted | | | | | | |
| Comparative Example 4 | No conducted | | | | | | |
| Comparative Example 5 | No conducted | | | | | | |
| Comparative Example 6 | No conducted | | | | | | |

| | Solvent distillation step | | | | | | |
|---|---|---|---|---|---|---|---|
| | Condition of distillation | | | | | | |
| | Kind of alkali & neutralization degree | | Pressure | Maximum liquid temperature Maximum liquid | Neutralization and distillation Solid | Non-neutralization and distillation Acyl amino | Distillation |
| Example | Alkali | Neutralization degree | Pressure mmHg | temperature °C. | content wt % | acid/water wt ratio | time Hr |
| Example 1 | TEA | 0.5 | 327 | 78 | 30 | — | 12 |
| Example 2 | KOH | 0.75 | 102 | 52 | 28 | — | 12 |
| Example 3 | NaOH | 0.75 | 214 | 68 | 25 | — | 12 |
| Example 4 | TEA | 0.5 | 163 | 62 | 30 | — | 3.5 |
| Example 5 | KOH | 0.75 | 83 | 48 | 28 | — | 3.5 |
| Example 6 | NaOH | 0.75 | 254 | 72 | 25 | — | 3.5 |
| Example 7 | TEA | 0.5 | 163 | 62 | 30 | — | 3.5 |
| Example 8 | None | None | 265 | 73 | — | 53/47 | 4 |
| Example 9 | None | None | 356 | 80 | — | 41/59 | 4 |
| Example 10 | None | None | 468 | 87 | — | 62/38 | 4 |
| Example 11 | None | None | 234 | 70 | — | 50/50 | 4 |
| Example 12 | None | None | 265 | 73 | — | 54/46 | 4 |
| Example 13 | None | None | 265 | 73 | — | 53/47 | 4 |
| Comparative Example 1 | TEA | 0.5 | 327 | 78 | 30 | — | 12 |
| Comparative Example 2 | TEA | 0.5 | Atmospheric pressure | 100 | 30 | — | 15 |
| Comparative Example 3 | NaOH | 0.75 | 187 | 65 | 55 | — | — |
| Comparative Example | None | None | Atmospheric | 105 | — | 100/0 | 15 |

TABLE 2-continued

| | | | | | | | | |
|---|---|---|---|---|---|---|---|---|
| Example 4 | | | pressure | | | | | |
| Comparative Example 5 | None | None | Atmospheric pressure | 110 | — | | 100/0 | 15 |
| Comparative Example 6 | TEA | 0.5 | 588 | 93 | 30 | | — | 12 |

TABLE 3

| | Long chain N-acyl acidic amino acid or its salt | | | | | |
|---|---|---|---|---|---|---|
| | | Impurities in acyl amino acid | | | | Odor of |
| | Acyl amino acid | Amount of remaining | Inorganic salts | | Free fatty | acyl aminate aqueous solution |
| Example | Yield % | TBA wt ppm | $Na_2SO_4$ wt % | NaCl wt % | acid wt % | Evaluation result |
| Example 1 | 96.5 | 60 | 0.044 | 0.063 | 2.3 | ○ |
| Example 2 | 97.0 | 62 | 0.12 | 0.09 | 1.7 | ○ |
| Example 3 | 96.8 | 70 | 0.006 | 0.009 | 1.9 | ○ |
| Example 4 | 97.1 | 50 | <0.004 | <0.001 | 1.7 | ○ |
| Example 5 | 97.1 | 70 | 0.006 | 0.009 | 1.6 | ○ |
| Example 6 | 97.0 | 75 | 0.006 | 0.009 | 1.7 | ○ |
| Example 7 | 97.0 | 51 | 0.043 | 0.060 | 1.7 | ○ |
| Example 8 | 97.0 | 50 | 0.006 | 0.009 | 1.8 | ○ |
| Example 9 | 96.8 | 60 | 0.006 | 0.009 | 1.9 | ○ |
| Example 10 | 96.6 | 60 | 0.006 | 0.009 | 2.1 | ○ |
| Example 11 | 97.1 | 65 | 0.12 | 0.052 | 1.8 | ○ |
| Example 12 | 97.0 | 65 | 0.11 | 0.060 | 1.8 | ○ |
| Example 13 | 96.8 | 55 | 0.19 | 0.095 | 1.9 | ○ |
| Comparative Example 1 | 86.5 | 60 | 0.64 | 0.63 | 12.3 | ○ |
| Comparative Example 2 | 92.3 | Acetone N.D. | 1.3 | 1.7 | 6.5 | X |
| Comparative Example 3 | — | 50000 | 0.93 | 0.70 | — | X |
| Comparative Example 4 | 92.3 | 80 | 0.64 | 0.63 | 6.5 | ○ |
| Comparative Example 5 | 90.5 | 60 | 0.92 | 0.70 | 8.3 | ○ |
| Comparative Example 6 | 95.3 | 60 | 0.64 | 0.63 | 3.5 | ○ |

TABLE 4

| | | Evaluation on 30% triethanolamine aqueous solution | | | | | Evaluation on shampoo composite liquid | | |
|---|---|---|---|---|---|---|---|---|---|
| | Test liquid | $Na_2SO_4$ (wt %) | NaCl (wt %) | Free fatty acid content (wt %) | Solidifying point (° C.) | Evaluation | Odor | State of liquid | Evaluation |
| Example 1 | Triethanol N-cocoyl-L-glutamate aqueous solution | 0.044 | 0.063 | 2.3 | −12.0 | ○ | ○ | Transparent even after six months | ○ |
| Example 4 | Triethanol N-cocoyl-L-glutamate aqueous solution | <0.044 | <0.001 | 1.7 | −13.0 | ○ | ○ | Transparent even after six months | ○ |
| Example 7 | Triethanol N-lauroyl-L-glutamate aqueous solution | 0.043 | 0.060 | 1.7 | −12.5 | ○ | — | — | — |
| Example 8 | Triethanol N-cocoyl-L-glutamate aqueous solution | 0.006 | 0.009 | 1.8 | −12.6 | ○ | — | — | — |

TABLE 4-continued

| | | Evaluation on 30% triethanolamine aqueous solution | | | | | Evaluation on shampoo composite liquid | | |
|---|---|---|---|---|---|---|---|---|---|
| | Test liquid | Na₂SO₄ (wt %) | NaCl (wt %) | Free fatty acid content (wt %) | Solidifying point (° C.) | Evaluation | Odor | State of liquid | Evaluation |
| Example 10 | Triethanol N-cocoyl-L-glutamate aqueous solution | 0.006 | 0.009 | 2.1 | −12.0 | ○ | — | — | — |
| Example 11 | Triethanol N-lauroyl-L-glutamate aqueous solution | 0.12 | 0.052 | 1.8 | −12.3 | ○ | — | — | — |
| Example 13 | Triethanol N-cocoyl-L-glutamate aqueous solution | 0.19 | 0.095 | 1.9 | −12.3 | ○ | — | — | — |
| Comparative Example 1 | Triethanol N-cocoyl-L-glutamate aqueous solution | 0.64 | 0.63 | 12.3 | −7.0 | X | — | — | — |
| Comparative Example 2 | Triethanol N-cocoyl-L-glutamate aqueous solution | 1.3 | 1.7 | 6.5 | −9.0 | X | X | Turbidity was observed one day after blending | X |
| Comparative Example 4 | Triethanol N-cocoyl-L-glutamate aqueous solution | 0.64 | 0.63 | 6.5 | −9.0 | X | — | — | — |
| Comparative Example 5 | Triethanol N-lauroyl-L-glutamate aqueous solution | 0.92 | 0.7 | 8.3 | −9.0 | X | — | — | — |
| Comparative Example 6 | Triethanol N-cocoyl-L-glutamate aqueous solution | 0.64 | 0.63 | 3.5 | −10.6 | ○ | ○ | Turbidity was observed one day after blending | X |

TABLE 5

| Composition | Amount blended (wt. part) |
|---|---|
| Triethanolamine N-cocoyl-L-glutamate aqueous solution | 34.5 |
| Lauryldimethylaminoacetic acid betaine | 12 |
| Coconut oil fatty acid diethanolamide | 5 |
| Cationic cellulose | 0.6 |
| 1,3-Butanediol | 0.5 |
| Purified water | Balance to make the whole |

What is claimed is:

1. A process for producing a N-($C_8$–$C_{20}$)-acyl acidic amino acid, comprising a washing step of removing impurities by separating a mixture of the N-($C_8$–$C_{20}$)-acyl acidic amino acid, which is obtained through the following steps, and which contains inorganic salts as impurities, and a medium consisting essentially of water and tertiary butanol into an aqueous layer and an organic layer containing the N-($C_8$–$C_{20}$)-acyl acidic amino acid at a temperature of from 35 to 80° C.:

1) an acylation reaction step of subjecting an acidic amino acid and a long chain fatty acid halide to condensation in a mixed solvent consisting essentially of water and tertiary butanol in the presence of an alkali, and
2) an acid precipitation separation step of adjusting a pH of the obtained reaction liquid to from 1 to 6 with a mineral acid to separate the mixture into an organic layer and an aqueous layer, thereby obtaining an organic layer containing the N-($C_8$–$C_{20}$)-acyl acidic amino acid.

2. The process according to claim 1, wherein the mixture in the washing step is adjusted to have a N-($C_8$–$C_{20}$)-acyl acidic amino acid concentration of from 0.001 to 55% by weight, a tertiary butanol concentration of from 5 to 45% by weight and a water concentration of from 20 to 99% by weight, thereby causing the separation.

3. The process according to claim 1 or 2, wherein a molar ratio of long chain fatty acid halide/acidic amino acid in the acylation reaction step is not more than 1.05.

4. The process according to claim 1 or 2, wherein the pH in the acid precipitation separation step is from 1 to 3.

5. The process according to claim 1 or 2, wherein the organic layer containing the N-($C_8$–$C_{20}$)-acyl acidic amino acid obtained in the washing step is subjected to removal of an organic solvent by distillation, in which not less than 1/20 of carboxyl groups in the N-($C_8$–$C_{20}$)-acyl acidic amino acid is converted into its alkali salt, and the distillation is carried out at a temperature not exceeding 90° C., and water is added to maintain a solid concentration of the mixed liquid to from 5 to 50% by weight.

6. The process according to claim 1 or 2, wherein the organic layer containing the N-($C_8$–$C_{20}$)-acyl acidic amino acid obtained in the washing step is subjected to removal of an organic solvent by distillation, wherein the temperature does not exceed 90° C., and water is added to maintain a weight ratio between the N-($C_8$–$C_{20}$)-acyl acidic amino acid and water within a range of from 35/65 to 65/35, provided that a content of the organic solvent in the mixed liquid is not more than 5% by weight.

7. The process according to claim 1 or 2, wherein in distillation-removing an organic solvent from the organic layer containing the N-($C_8$–$C_{20}$)-acyl acidic amino acid obtained in the washing step, the distillation-removal of an organic solvent is carried out using a spray evaporator, wherein the mixture is formed into a vapor-liquid mixed-phase, which is then sprayed into an evaporation can to evaporate the solvent.

8. A composition, which comprises:
   a N-($C_8$–$C_{20}$)-acyl acidic amino acid or a salt thereof;
   an inorganic salt of not more than 1% by weight; and
   tertiary butanol of from 0.1 to 750 ppm by weight, said contents being based on the weight of the N-($C_8$–$C_{20}$)-acyl acidic amino acid.

9. The composition according to claim 8, which has a content of a free fatty acid of not more than 3.0% by weight based on the weight of the N-($C_8$–$C_{20}$)-acyl acidic amino acid.

10. The composition according to claim 8 or 9, which is obtained by a reaction between an acidic amino acid and a long chain fatty acid halide in a mixed solvent consisting essentially of tertiary butanol and water.

11. The composition according to claim 8 or 9, which is obtained according to a process comprising a washing step of removing an inorganic salt by separating a mixture composed of the N-($C_8$–$C_{20}$)-acyl acidic amino acid containing an inorganic salt and a medium consisting essentially of water and tertiary butanol into an aqueous layer and an organic layer containing the N-($C_8$–$C_{20}$)-acyl acidic amino acid at a temperature of from about 35 to 80° C.

12. The composition according to claim 8 or 9, which is obtained through the following steps:
   1) an acylation reaction step of subjecting an acidic amino acid and a long chain fatty acid halide to condensation in a mixed solvent consisting essentially of water and tertiary butanol in the presence of an alkali,
   2) an acid precipitation separation step of adjusting a pH of the obtained reaction liquid to from 1 to 6 with a mineral acid to separate into an organic layer and an aqueous layer, thereby obtaining an organic layer containing the N-($C_8$–$C_{20}$)-acyl acidic amino acid, and
   3) a washing step of removing impurities by mixing the obtained organic layer with water and/or tertiary butanol to separate into an aqueous layer and an organic layer containing the N-($C_8$–$C_{20}$)-acyl acidic amino acid at a temperature of from 35 to 80° C.

13. The composition according to claim 8 or 9, which is obtained through the following steps:
   1) an acylation reaction step of subjecting an acidic amino acid and a long chain fatty acid halide to condensation in a mixed solvent consisting essentially of water and tertiary butanol in the presence of an alkali,
   2) an acid precipitation separation step of adjusting a pH of the obtained reaction liquid to from 1 to 6 with a mineral acid to separate into an organic layer and an aqueous layer, thereby obtaining an organic layer containing the N-($C_8$–$C_{20}$)-acyl acidic amino acid,
   3) a washing step of removing impurities by mixing the obtained organic layer with water and/or tertiary butanol to separate into an aqueous layer and an organic layer containing the N-($C_8$–$C_{20}$)-acyl acidic amino acid at a temperature of from 35 to 80° C., and
   4) a neutralization and solvent distillation removal step of subjecting the organic layer containing the N-($C_8$–$C_{20}$)-acyl acidic amino acid obtained in the washing step to removal of an organic solvent by distillation, in which no less than 1/20 of carboxyl groups of the N-($C_8$–$C_{20}$)-acyl acidic amino acid is converted into its alkali salt, and the distillation is carried out under conditions that a temperature of a resulting mixed liquid is controlled as not to exceed 90° C., and water is added to maintain a solid concentration of the mixed liquid of from 5 to 50% by weight.

14. The composition according to claim 8 or 9, which is obtained through the following steps:
   1) an acylation reaction step of subjecting an acidic amino acid and a long chain fatty acid halide to condensation in a mixed solvent consisting essentially of water and tertiary butanol in the presence of an alkali,
   2) an acid precipitation separation step of adjusting a pH of the obtained reaction liquid to from 1 to 6 with a mineral acid to separate into an organic layer and an aqueous layer, thereby obtaining an organic layer containing the N-($C_8$–$C_{20}$)-acyl acidic amino acid,
   3) a washing step of removing impurities by mixing the obtained organic layer with water and/or tertiary butanol to separate into an aqueous layer and an organic layer containing the N-($C_8$–$C_{20}$)-acyl acidic amino acid at a temperature of from 35 to 80° C., and
   4) a neutralization and solvent distillation removal step of subjecting the organic layer containing the N-($C_8$–$C_{20}$)-acyl acidic amino acid obtained in the washing step to removal of an organic solvent by distillation, which is carried out under conditions that a temperature is controlled as not to exceed 90° C., and water is added to maintain a weight ratio between the N-($C_8$–$C_{20}$)-acyl acidic amino acid and water within a range of from 35/65 to 65/35, provided that a content of the organic solvent in the mixed liquid is not more than 5% by weight.

15. A liquid or solid cosmetic composition, which comprises a N-($C_8$–$C_{20}$)-acyl acidic amino acid or a salt thereof having a content of an inorganic salt of not more than 1% by weight and a content of tertiary butanol of from 0.1 to 750 ppm by weight, said contents being based on the weight of the N-($C_8$–$C_{20}$)-acyl acidic amino acid.

16. A liquid or solid cosmetic composition, which comprises a N-($C_8$–$C_{20}$)-acyl acidic amino acid or a salt thereof having a content of an inorganic salt of not more than 1% by weight and a content of tertiary butanol of from 0.1 to 750 ppm by weight, an a content of a free fatty acid of not more than 3.0% by weight, said contents being based on the weight of the N-($C_8$–$C_{20}$)-acyl acidic amino acid.

17. A detergent composition, which comprises a N-($C_8$–$C_{20}$)-acyl acidic amino acid or a salt thereof having a content of an inorganic salt of not more than 1% by weight and a content of tertiary butanol of from 0.1 to 750 ppm by weight, said contents being based on the weight of the N-($C_8$–$C_{20}$)-acyl acidic amino acid.

18. A detergent composition, which comprises a N-($C_8$–$C_{20}$)-acyl acidic amino acid or a salt thereof having a content of an inorganic salt of not more than 1% by weight and a content of tertiary butanol of from 0.1 to 750 ppm by weight, an a content of a free fatty acid of not more than 3.0% by weight, said contents being based on the weight of the N-($C_8$–$C_{20}$)-acyl acidic amino acid.

* * * * *